US008933036B2

(12) United States Patent
Dal Farra et al.

(10) Patent No.: US 8,933,036 B2
(45) Date of Patent: Jan. 13, 2015

(54) COSMETIC AND/OR PHARMACEUTICAL COMPOSITION COMPRISING A YEAST PEPTIDE HYDROLYSATE AND USE OF THE YEAST PEPTIDE HYDROLYSATE AS AN ACTIVE AGENT FOR STRENGTHENING HAIR

(71) Applicants: Claude Dal Farra, Kerhonkson, NY (US); Nouha Domloge, Valbonne (FR); Jean-Marie Botto, Valbonne (FR); Catherine Gondran, Seillans (FR); Corinne Coquet, Cipieres (FR); Frederique Portolan, Valbonne (FR)

(72) Inventors: Claude Dal Farra, Kerhonkson, NY (US); Nouha Domloge, Valbonne (FR); Jean-Marie Botto, Valbonne (FR); Catherine Gondran, Seillans (FR); Corinne Coquet, Cipieres (FR); Frederique Portolan, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 13/843,452

(22) Filed: Mar. 15, 2013

(65) Prior Publication Data
US 2013/0296251 A1 Nov. 7, 2013

Related U.S. Application Data

(63) Continuation-in-part of application No. 13/505,348, filed as application No. PCT/FR2010/000724 on Nov. 2, 2010, now abandoned, application No. 13/843,452, which is a continuation-in-part of application No. 13/264,035, filed as application No. PCT/FR2010/000311 on Apr. 15, 2010, now Pat. No. 8,674,072.

(30) Foreign Application Priority Data

Apr. 15, 2009 (FR) .................................... 09 01822
Nov. 3, 2009 (FR) .................................... 09 05257

(51) Int. Cl.
*A61K 38/00* (2006.01)
*A61P 17/00* (2006.01)
*A61K 8/64* (2006.01)
*A61Q 5/00* (2006.01)
*A61Q 7/00* (2006.01)

(52) U.S. Cl.
CPC ... *A61K 8/64* (2013.01); *A61Q 5/00* (2013.01); *A61Q 7/00* (2013.01)
USPC ........................................................ 514/18.8

(58) Field of Classification Search
CPC .............. A61K 8/64; A61Q 5/00; A61Q 7/00
See application file for complete search history.

(56) References Cited

U.S. PATENT DOCUMENTS

| 4,139,619 | A | 2/1979 | Chidsey, III |
| 4,596,812 | A | 6/1986 | Chidsey, III et al. |
| 5,733,558 | A | 3/1998 | Breton et al. |
| 5,977,082 | A | 11/1999 | Gatti et al. |
| 7,431,919 | B2 | 10/2008 | Travkina et al. |
| 7,887,858 | B2 | 2/2011 | Cauchard et al. |
| 8,394,390 | B2 | 3/2013 | Galeotti et al. |
| 2004/0141939 | A1 | 7/2004 | Dal Farra et al. |
| 2005/0272097 | A1 | 12/2005 | Calenoff |
| 2007/0274937 | A1 | 11/2007 | Dal Farra et al. |
| 2008/0268077 | A1 | 10/2008 | Vielhaber |

FOREIGN PATENT DOCUMENTS

| EP | 0265099 | | 4/1988 |
| EP | 0327263 | | 8/1989 |
| EP | 0695801 | | 2/1996 |
| EP | 0738510 | | 10/1996 |
| EP | 0902035 | | 3/1999 |
| EP | 1152062 | | 11/2001 |
| EP | 1281401 | | 2/2003 |
| EP | 1272148 | | 6/2006 |
| EP | 1707189 | | 10/2006 |
| FR | 2789312 | | 8/2000 |
| FR | 2868309 | | 10/2005 |
| FR | 2887772 | | 1/2007 |
| FR | 2904552 | | 2/2008 |
| FR | 2911779 | | 8/2008 |
| FR | 2915384 | | 10/2008 |
| FR | 2925325 | | 6/2009 |
| FR | 2925326 | | 6/2009 |
| FR | 2925327 | | 6/2009 |
| FR | 2925330 | | 6/2009 |
| FR | 2927254 | | 8/2009 |
| FR | 2927254 | A1 * | 8/2009 |
| JP | 07-316023 | | 12/1995 |
| WO | 03/008438 | | 1/2003 |
| WO | 03/023067 | | 3/2003 |
| WO | 03/068184 | | 8/2003 |
| WO | 03/087831 | | 10/2003 |
| WO | 2004/031211 | | 4/2004 |
| WO | 2004/058282 | | 7/2004 |

(Continued)

OTHER PUBLICATIONS

Trueb R "Pharmacologic interventions in aging hair" Clinical Interventions in Aging 1:121-129. Published 2006.*
Office Action, U.S. Appl. No. 13/264,035 (Jul. 10, 2013).
Office Action, U.S. Appl. No. 13/505,348 (Sep. 12, 2012).
Office Action, U.S. Appl. No. 13/505,348 (Apr. 9, 2013).
International Search Report, International Application No. PCT/FR2010/000724 (Mar. 3, 2011).
International Preliminary Report on Patentability, International Application No. PCT/FR2010/000724 (Jun. 5, 2012).

(Continued)

*Primary Examiner* — Maury Audet
*Assistant Examiner* — Zachary J Miknis
(74) *Attorney, Agent, or Firm* — Thompson Hine L.L.P.

(57) ABSTRACT

A method of attenuating hair loss includes applying to the hair a composition having an effective amount of a hair-loss attenuating peptide hydrolysate and a cosmetically acceptable carrier.

15 Claims, 24 Drawing Sheets

(56) References Cited

FOREIGN PATENT DOCUMENTS

| WO | 2004/096168 | 11/2004 |
|----|-------------|---------|
| WO | 2005/047328 | 5/2005 |
| WO | 2005/080985 | 9/2005 |
| WO | 2005/107697 | 11/2005 |
| WO | 2005/111081 | 11/2005 |
| WO | 2008/015343 | 2/2008 |

OTHER PUBLICATIONS

International Preliminary Report on Patentability, International Application No. PCT/FR2010/000311 (Nov. 22, 2011).
International Search Report, International Application No. PCT/FR2010/000311 (mailed Jul. 6, 2010; published Oct. 21, 2010).
"Designing Custom Peptides," from SIGMA Genosys, http://www.sigma-genosys.com/peptide_design.asp, pp. 1-2, (accessed Dec. 16, 2004).
Alopecia from Merck Manual, pp. 1-5 (accessed Jul. 2, 2013).
Berendsen, H.J.C., "A Glimpse of the Holy Grail?" Science, 1998, 282: 642-643.
Birch, M.P. et al., "Hair density, hair diameter and the prevalence of female pattern hair loss," British Journal of Dermatology, 144, pp. 297-304 (2001).
Bradley, C.M. et al., "Limits of Cooperativity in a Structurally Modular Protein: Response of the Notch Ankyrin Domain to Analogous Alanine Substitutions in Each Repeat," J. Mol. Biol., 2002, 324: 373-386.
Chronic Effects of Sunlight, Merck Manual, pp. 1-2 (accessed Aug. 23, 2012).
Courtois, M. et al., "Ageing and hair cycles," British Journal of Dermatology, 132, pp. 86-93 (1995.
Dal Farra et al., Machine translation of FR 2904552, pp. 1-16 (Aug. 3, 2006).
Dal Farra et al., Machine translation of FR 2915384, pp. 1-8 (Apr. 27, 2007).
Definition of "derivative" from http://cancerweb.ncl.ac.uk/omd/about.html, pp. 1-5 (accessed Jul. 7, 2005).
Effects of Aging on the Skin, Merck Manual, p. 1 (accessed Apr. 9, 2012).
Ghadially, R. et al., "The Aged Epidermal Permeability Barrier," The Journal of Clinical Investigations, Inc., vol. 95, pp. 2281-2290 (May 1995).
Gourley, D.G et al., "HMG-CoA Reductase: a Novel Target for Antimicrobial Chemotherapy," Abstracts of the Interscience Conference on Antimicrobial Agents and Chemotherapy, vol. 43, 2003, p. 219, XP035587 & 43rd Annual Interscience Conference on Antimicrobial Agents and Chemotherapy, Chicago, IL, USA, Sep. 14-17, 2003 (abstract).
Kullmann, W., "Proteases as Catalysts for Enzymic Syntheses of Opioid Peptides," The Journal of Biological Chemistry, vol. 255, No. 17, pp. 8234-8238 (Sep. 10, 1980).
Langbein, L. et al., "The Catalog of Human Hair Keratins," The Journal of Biological Chemistry, vol. 276, No. 37, pp. 35123-35132 (Sep. 14, 2001).
Lenoir, M.-C. et al., "Outer Root Sheath Cells of Human Hair Follicle are Able to Regenerate a Fully Differentiated Epidermis in Vitro," Developmental Biology, vol. 130, pp. 610-620 (1988).
Luskey, K.L. et al., "Human 3-Hydroxy-3-methylglutaryl Coenzyme A Reductase," The Journal of biological Chemistry, vol. 260, No. 18, pp. 10271-10277 (Aug. 25, 1985).
Martini, M.C., "Biochemical Analysis of epidermal lipids," Pathologie Biologie, 51, pp. 267-270 (2003).
Menon, G.K. et al., "De novo sterologenesis in the skin. II. Regulation by cutaneous barrier requirements," Journal of Lipid Research, vol. 26, pp. 418-427 (1985).
Ngo, J.T. et al., "Computational Complexity Protein Structure Prediction, and the Levinthal Paradox," The Protein Folding Problem and Tertiary Structure Prediction, K. Merc Jr. and S. Le Grand Edition, 1994, pp. 491-495.
Norlén, L. et al., "Inter- and Intra-Individual Differences in Human Stratum Corneum Lipid Content Related to Physical Parameters of Skin Barrier Function In Vivo," J. Invest. Dermatol., 112 (1), pp. 72-77 (1999).
Pelfini, C. et al., "Cheveux et vieillissement," J. Méd. Esth. et Chir. Derm., vol. XIV, No. 53, pp. 9-14 (Mar. 1987).
Porter, R.M. et al., "Keratin K6irs is specific to the inner root sheath of hair follicles in mice and humans," British Journal of Dermatology, 145, pp. 558-568 (2001).
Proksch, E. et al., "Barrier function regulates epidermal lipid and DNA synthesis," British Journal of Dermatology, 128, pp. 473-482 (1993).
Rudinger, J., "Characteristics of the amino acids as components of a peptide hormone sequence," Peptide Hormones, J.A. Parsons Edition, University Party Press, Jun. 1976, pp. 1-7.
Schinzel, R. et al., "The phosphate recognition site of *Escherichia coli* maltodextrin phosphorylase," FEBS, Jul. 1991, 286(1,2): 125-128.
SEQ ID No. 30601 from U.S. Patent 8,394,390 (Mar. 12, 2013).
Voet, D. et al., Biochemistry, Second Edition, John Wiley & Sons, Inc., 1995, pp. 235-241.

* cited by examiner

Mean values of A/T ratio calculated for the baseline and after 30, 60 and 90 days of the products use for both study groups. Main ± standard deviation.

FORMULATION

Conditioning Milk Spray with Dynagen™
Formula #11994-20

| Ingredients (INCI/Commercial Name) | % P/P | Function | Supplier |
|---|---|---|---|
| Deionized Water | 92.48 | Vehicle | |
| Polyquaternium-11 | 3.50 | Conditioner | ISP |
| PEG/PPG-25/25 Dimethicone | 1.00 | Conditioner | ISP |
| Propylene Glycol (and) Diazolidinyl Urea (and) Iodopropynyl Butylcarbamate | 0.50 | Preservative | ISP |
| Sodium Polyacrylate (and) Hydrogenated Polydecene (and) Trideceth-6 | 0.32 | Viscosity Agent | ISP |
| Styrene/VP Copolymer | 1.00 | Opaquing | ISP |
| Water (and) Glycerin (and) Hydrolyzed Yeast Protein (Dynagen™) | 1.00 | Active agent against hair loss | ISP |
| Premix | | | |
| Oleth-20 | 0.10 | Solublizer | Croda |
| Fragrance | 0.10 | perfume | Ungerer |
| Total | 100.00 | | |

FIG. 2

Figure 3 illustrates some examples of the typical morphological aspects of the hair fibers observed in the trichogram.

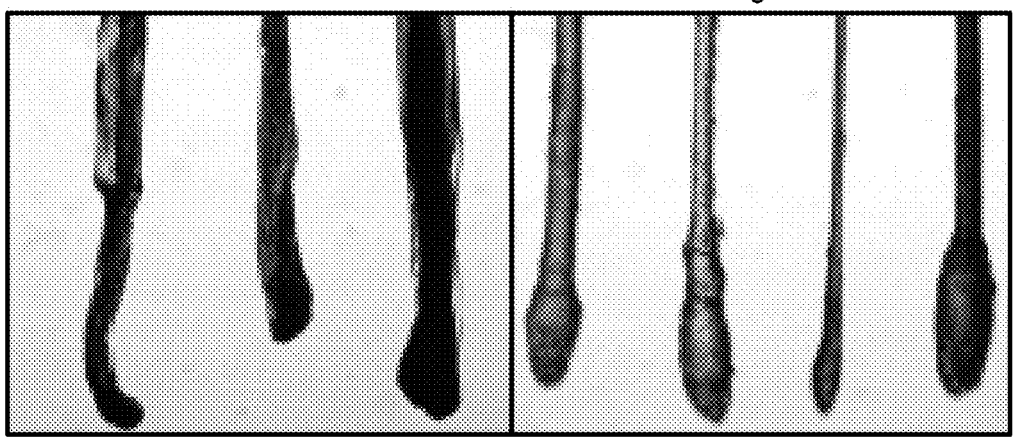

(A)  (B)

Typical morphological aspects for hair strands in the anagen(A) and telogen(B) phase.

FIG. 3

Anti-hair fall

- Hair loss
  - Average life of a hair strand is 4.5 years
  - Approximately 70-100 hairs are shed daily
- Hair follicle cycle: growth, regression, rest
  - Growth phase: Anagen (2-6 years) 90% hair
  - Regression phase: Catagen (2-4 weeks) 1% hair
  - Rest phase: Telogen (2-4 months) 10% hair Dynagen™: Inner Strength & Nourishment
- Boosts markers that influence the performance
  – keratin-14
  – keratin-17
  – keratin-71
  – collagen I
  – collagen IV
  – CD34
  – trichohyalin

Dynagen™: Inner Strength & Nourishment

Protocol

Material: Hairline skin

Preparation: 6mm punch biopsies

Product application: Dynagen at 1% (topical application)

Application time: Once per day for two days

Evaluation: Immunofluorescence; evaluated markers appear in green fluorescence; cell nuclei are stained in blue by DAPI

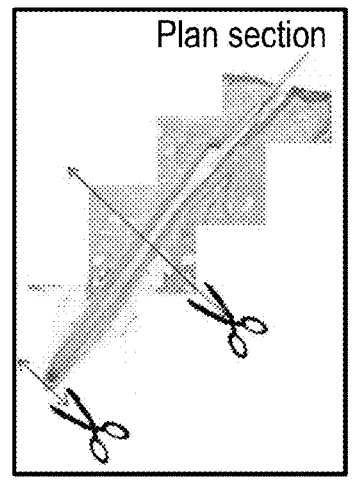

FIG. 7

Dynagen™: Inner Strength & Nourishment
Keratin-14 expression increases in ORS paraffin sections (ex-vivo)

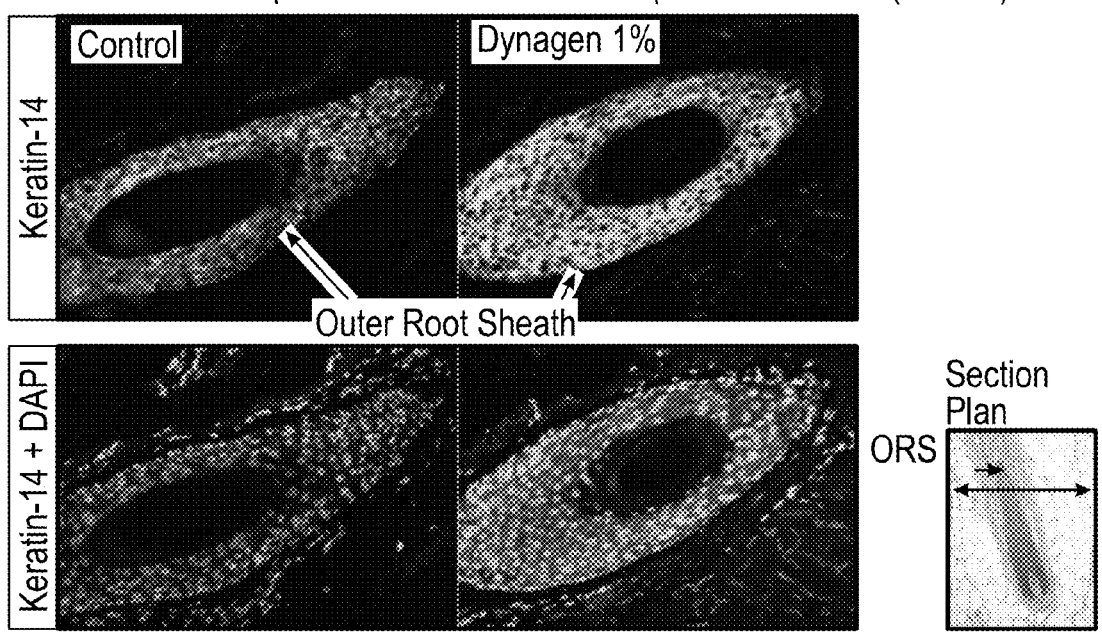

FIG. 8

Dynagen increases trichohyalin (IRS) in paraffin section
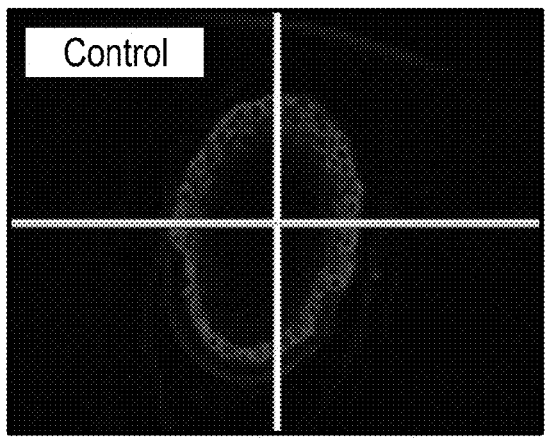
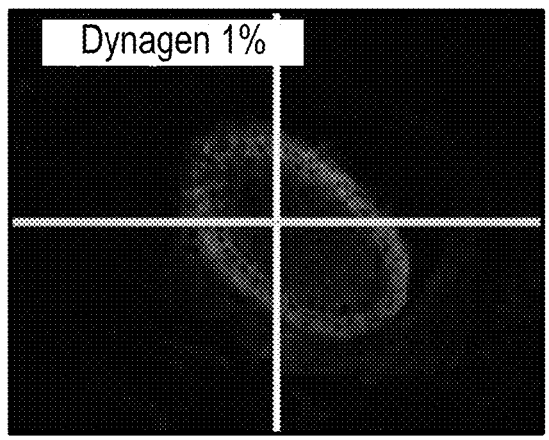
Dynagen increases K71 (IRS) in paraffin section
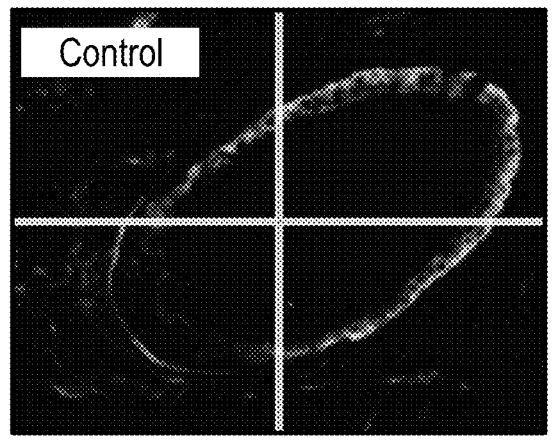
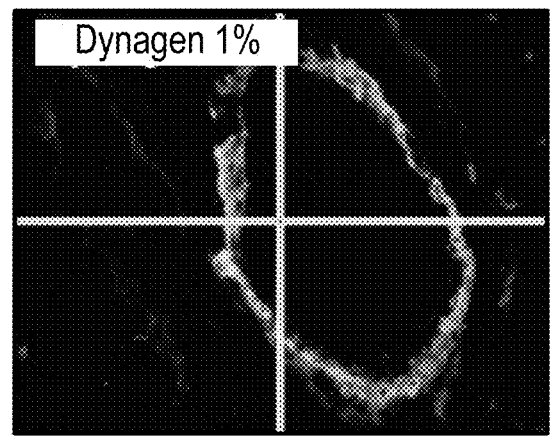
FIG. 11

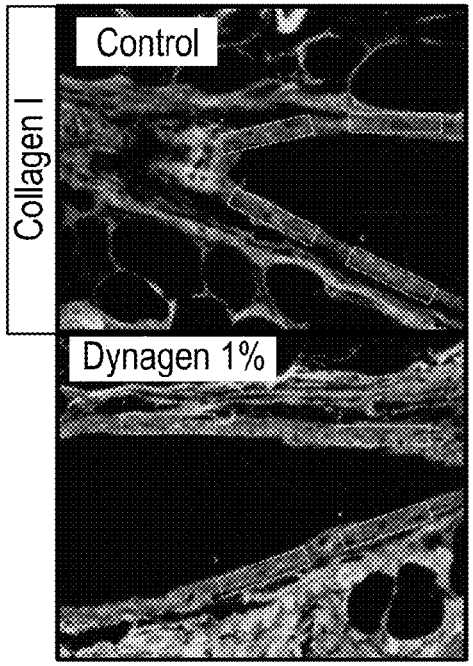 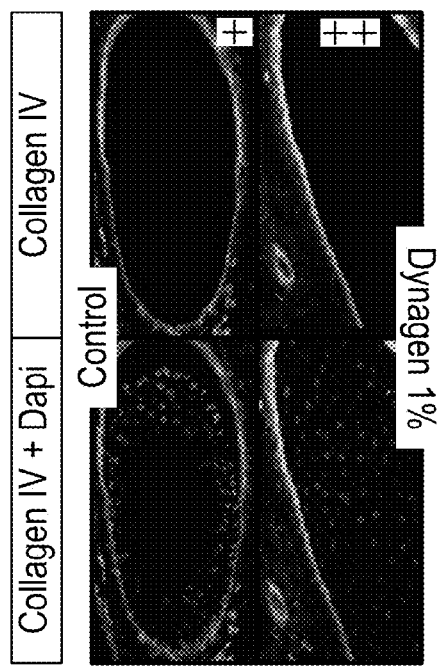

FIG. 12

Dynagen™ - Summary

- By boosting the keratin-14 and keratin-17 expression (ex-vivo), Dynagen may help optimize the hair structure and its strength.
- Boosting both CD34 and collagen IV expression, Dynagen may help to improve the nutrition and the healthy appearance of hair.
- By boosting the ex-vivo expression of collagen I, Dynagen may help optimize hair follicle strength and help ensure cohesion to maintain and preserve the hair follicle structure.

FIG. 13

Conditioning spray milk

| | Formula 11749-136 | | |
|---|---|---|---|
| | Ingredients (INCI/Trade name) | %W/W | Supplier |
| | Deionized Water | 92.68 | |
| Cond. | Polyquaternium-11/Gafquat® 755N | 3.50 | ISP |
| | PEG/PPG-25/25 Dimethicone /SiTec DMC 6031 | 1.00 | ISP |
| Pres. | Propylene Glycol (and) Diazolidinyl Urea (and) Iodopropynyl Butylcarbamate/Liquid Germall® Plus | 0.50 | ISP |
| Thick. | Sodium Polyacrylate (and) Hydrogenated Polydecene (and) Trideceth-6/ RapiThix™ A-60 | 0.32 | ISP |
| Opacif. | Polectron 430 | 1.00 | ISP |
| | Dynagen Dynagen | 1.00 | ISP |
| | Total | 100.00 | |

- Usage
  - Apply product on scalp when hair is damp. Massage into scalp and distribute product throughout the hair. Style hair as usual.
- Benefit space
  - Leaves hair feeling smooth and conditioned and allows for easy wet combing.

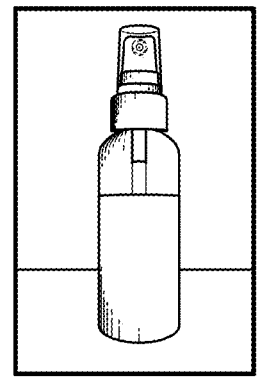

FIG. 14

Hair and Scalp Nourisher cream

| | Formula 11749-132 | | |
|---|---|---|---|
| | Ingredients (INCI/Trade name) | %W/W | Supplier |
| | Phase A | | |
| | Deionized Water | 71.81 | |
| | Aminomethyl Propanol | 0.05 | Angus |
| Thick. | Acrylic Acid/VP Crosspolymer/UltraThix™ P-100 | 0.45 | ISP |
| | Phase B | | |
| Prod. sens | Gycerol Dilaurate/Emulsynt™ GDL | 0.25 | ISP |
| | Jojoba Seed Oil | 1.00 | Lipo |
| | Cetearyl Alcohol | 2.00 | Rita |
| Emuls | Glyceryl Stearate (and) Laureth-23 /Cerasynt 945 | 0.50 | ISP |
| | Phase C | | |
| Cond. | Cyclopentasiloxane/SiTec™ CM040 | 0.25 | ISP |
| | Phase D | | |
| Film f. | Copolymer 845 | 2.00 | ISP |
| | Water | 20.00 | |
| | Aminomethyl Propanol | 0.19 | Angus |
| | Phase E | | |
| Pres | LGP | 0.50 | ISP |
| | Dynagen Dynagen | 1.00 | ISP |
| | Total | 100.00 | |

• Benefit space
 — Leaves hair feeling smooth and conditioned and allows for easy wet combing. Style hair as usual. Allows for durable style and adds to shine.

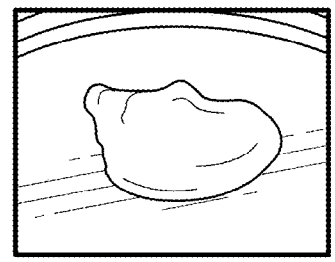

FIG. 15

Activity of Dynagen in the product

| Dynagen | Formula | Selected marker | Effect |
|---|---|---|---|
| Dynagen Dynagen | Conditioning spray milk | K14 | ++ |
| | Hair and scalp nourisher | K14 | ++ |

FIG. 16

Anti-hair Fall clinical studies
- Objective
  — Evaluate the efficacy of the Conditioning Spray Milk with Dynagen™ applied to scalp in order to prevent hair fall
- Products tested
  — Experimental Group: Formulation* with Dynagen™
  — Control Group: Formulation without Dynagen™
- Clinical studies
  — Short term 1-month study with total 30ish Panelists
    - Panelists did not color hair during study
  — Long term 3-month study with total 70ish Panelists
    - Panelists were allowed to color their hair once - half way into the study
- Venue
  — Sao Paulo, Brazil

FIG. 17

Formulation

Conditioning Spray Milk with Dynagen : <u>Experimental</u>

| Ingredients (INCI/Trade name) | % W/W | Supplier |
|---|---|---|
| Deionized Water | 92.48 | |
| Polyquaternium-11/Gafquat®755N | 3.50 | ISP |
| PEG/PPG-25/25 Dimethicone / Belsil DMC 6031 | 1.00 | Wacker |
| Propylene Glycol (and) Diazolidinyl Urea (and) Iodopropynyl Butylcarbamate/Liquid Germall®Plus | 0.50 | ISP |
| Sodium Polyacrylate (and) Hydrogenated Polydecene (and) Trideceth-6/RapiThix™ A-60 | 0.32 | ISP |
| Styrene/VP Copolymer/Antara®/Polectron® 430 | 1.00 | ISP |
| Water (and) Glycerin (and) Hydrolyzed Yeast Protein/ Dynagen™ | 1.00 | ISP |
| Premix | | |
| Oleth-20/BRIJ O20 | 0.10 | Croda |
| Fragrance/Night Blooming Orchid XX19-00529 | 0.10 | Ungerer |
| Total | 100.00 | |

Procedure
1. Charge water to a suitable mixing vessel and begin agitation.
2. Add Gafquat 755N, Belsil DMC 6031 and Liquid Germall Plus one by one with mixing.
3. Add RapiThix A-60 and mix until uniform; which is at least for fifteen minutes.
4. Add Polectron and Dynagen and mix until uniform.
5. <u>Premix</u>: In a separate container, add Brij O20 and warm to 40°C. When it melts, add fragrance to it and mix until uniform and clear. Then add Premix to the main batch.

Typical Properties

| Appearance | White, Opaque Liquid |
|---|---|
| pH | 6.80 |
| Viscosity | Less than 100 cps |

FIG. 18

Formulation

Conditioning Spray Milk without Dynagen : Control

| Ingredients (INCI/Trade name) | % W/W | Supplier |
|---|---|---|
| Deionized Water | 93.48 | |
| Polyquaternium-11/Gafquat®755N | 3.50 | ISP |
| PEG/PPG-25/25 Dimethicone / Belsil DMC 6031 | 1.00 | Wacker |
| Propylene Glycol (and) Diazolidinyl Urea (and) Iodopropynyl Butylcarbamate/Liquid Germall®Plus | 0.50 | ISP |
| Sodium Polyacrylate (and) Hydrogenated Polydecene (and) Trideceth-6/RapiThix™ A-60 | 0.32 | ISP |
| Styrene/VP Copolymer/Antara®/Polectron® 430 | 1.00 | ISP |
| Water (and) Glycerin (and) Hydrolyzed Yeast Protein/ Dynagen™ | - | ISP |
| Premix | | |
| Oleth-20/BRIJ 020 | 0.10 | Croda |
| Fragrance/Night Blooming Orchid XX19-00529 | 0.10 | Ungerer |
| Total | 100.00 | |

Procedure
1. Charge water to a suitable mixing vessel and begin agitation.
2. Add Gafquat 755N, Belsil DMC 6031 and Liquid Germall Plus one by one with mixing.
3. Add RapiThix A-60 and mix until uniform; which is at least for fifteen minutes.
4. Add Polectron and Dynagen and mix until uniform.
5. Premix: In a separate container, add Brij 020 and warm to 40°C. When it melts, add fragrance to it and mix until uniform and clear. Then add Premix to the main batch.

Typical Properties

| Appearance | White, Opaque Liquid |
|---|---|
| pH | 5.80 |
| Viscosity | Less than 100 cps |

FIG. 19

Study design - Short Term (1-month)
- Design
  - Double blind with Control (w/o Dynagen™) and Experimental (w Dynagen™) groups.
  - Panelists had no chemical treatments on scalp 48h before study.
  - Duration 1 month. Panelists did not color hair during study.
- Panelists
  - N=29 (Control Group 16 Panelists; Experimental Group 13 Panelists)
  - All female
- Application
  - Panelists were trained to self apply product to scalp using a syringe.
  - They applied 8g product; minimum 5 days/week after shampoo & conditioner*.

FIG. 20

Study design - Long Term (3-month)
- Design
  - Double blind with Control (w/o DynagenTM) and Experimental (w DynagenTM) groups.
  - Panelists had no chemical treatments on scalp 48h before study.
  - Duration 3 months. Panelists had an option to color hair once during study.
- Panelists
  - N=74 (Control Group 39 Panelists; Experimental Group 35 Panelists)
  - All female
- Application
  - Panelists were trained to self apply product to scalp using a syringe.
  - They applied 8g product; minimum 5 days/week after shampoo/conditioner*.

*Panelists used their own shampoo and conditioner

FIG. 21

Methodology

1. Trichogram : Anagen to Telogen (A/T) ratio

— 50 hair strands are collected random from each subject.

— The bulb is assessed with an optical microscopy to determine the stage of the strand's life cycle and number of strands in the telogen and anagen phases.

▷ Increase in A/T ratio ⟶ decrease in hair fall

Methodology

2. Questioner
— Panelists were asked to filled a questioner after:
  - Short term 30 days
  - Long term 30, 60, and 90 days

FIG. 23

Anti-Hair Fall clinical study - Long Term (3-months)

| Control Group (product without biofunctional) | | Experimental Group (product with biofunctional) | |
|---|---|---|---|
| Day 0 | — Trichogram A/T ratio<br>— Scalp Examination<br>— Questionnaire | Day 0 | — Trichogram A/T ratio<br>— Scalp Examination<br>— Questionnaire |
| Day 1 | — Start Application<br>5 days/week | Day 1 | — Start Application<br>5 days/week |
| Day 30 | — Trichogram A/T ratio<br>— Scalp Examination<br>— Questionnaire | Day 30 | — Trichogram A/T ratio<br>— Scalp Examination<br>— Questionnaire |
| Day 60 | — Trichogram A/T ratio<br>— Scalp Examination<br>— Questionnaire | Day 60 | — Trichogram A/T ratio<br>— Scalp Examination<br>— Questionnaire |
| Day 90 | — Trichogram A/T ratio<br>— Scalp Examination<br>— Questionnaire<br>— Consumer Feedback | Day 90 | — Trichogram A/T ratio<br>— Scalp Examination<br>— Questionnaire<br>— Consumer Feedback |

Results
Control Group vs. Experimental Group
Change in A/T ratio after 1, 2 and 3 months of use

FIG. 24

The coefficient between the A/T ratio obtained in 30 days of evaluation and the baseline A/T raio, called CA/T, was obtained for both samples, as described in the following equation:

$CA/T = (A/T)tx / (A/T)ti$, where i=baseline and x=30 days.

The values for CA/T of both products were statistically compared using Student's t-test.

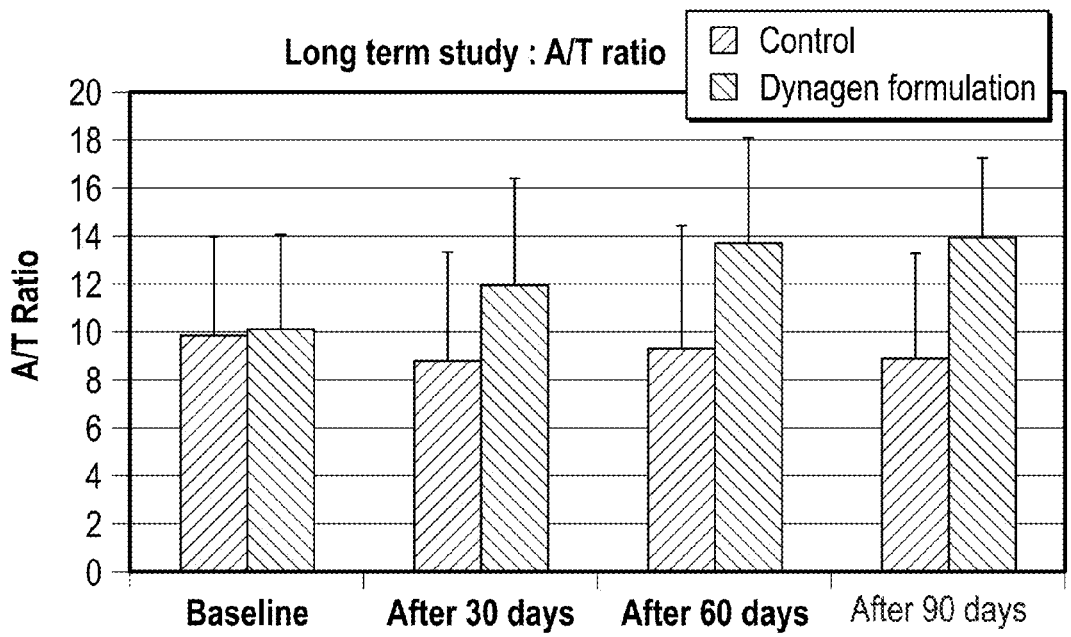

The coefficient between the A/T ratio obtained in 30, 60 or 90 days of evaluation and the baseline A/T raio, called CA/T, was obtained for both samples, as described in the following equation:

$CA/T = (A/T)tx / (A/T)ti$, where i=baseline and x=30, 60 or 90 days.

The values for CA/T of both products were statistically compared using Student's t-test.

FIG. 26

Summary: A/T ratio
- Results are based on t-Tests of the changes in A/T ratios from baseline levels of the Experimental and Control groups.

|  | Short term 30 days | Long term | | |
|---|---|---|---|---|
|  |  | 30 days | 60 days | 90 days |
| Experimental vs. Control | 83.28%# | 98.98%** | 99.87%*** | >99.99%*** |

▷ Directional trend was observed in the short term study.
▷ The cumulative effect of Dynagen™ can be observed in the long term study: increasing order of significances with respect to 30, 60 and 90 days.

FIG. 27

Panelists interview after 30 days, n=3

- Trichogram measurement
  - "Before the study it was less painful."
  - "After the 1 month study lot more painful" - which indicates product is working

- "In three weeks my husband/mother commented on my hair" - positive

- Panelists comment - *"Near the root hair feels fuller and thicker."* Not at the tips - considering the hair growth rate, it would take couple of weeks to see the effect at the tips.

- Key indicators: *"less hair in the drain, less hair on the floor (noticeable difference while cleaning the floor)"*

FIG. 33

Conclusion

- Trichogram measurement confirmed that Dynagen™ formulation delivered significant anti-hair fall effect.
- Panelists started observing noticeable anti-hair fall effect in 3 weeks time.
- The anti-hair fall effect was consumer perceivable.

FIG. 34

COSMETIC AND/OR PHARMACEUTICAL COMPOSITION COMPRISING A YEAST PEPTIDE HYDROLYSATE AND USE OF THE YEAST PEPTIDE HYDROLYSATE AS AN ACTIVE AGENT FOR STRENGTHENING HAIR

This application is a continuation-in-part to U.S. application Ser. No. 13/505,348 filed May 1, 2012, which is the National Stage Entry of International Application Serial No. PCT/FR10/00724 filed Nov. 2, 2010, which claims priority to French Application Serial No. 0905257 filed Nov. 3, 2009. This application is also a continuation-in-part to U.S. application Ser. No. 13/264,035 filed Oct. 12, 2011, which is the National Stage Entry of International Application Serial No. PCT/FR10/00311 filed Apr. 15, 2010, which claims priority to French Application Serial No. 0901822 filed Apr. 15, 2009. Each patent application identified above is incorporated here by reference in its entirety to provide continuity of disclosure.

The present disclosure is in the cosmetic and derma-pharmaceutical fields. The disclosure concerns the use of a composition comprising at least one yeast (*Saccharomyces cerevisiae*) peptide hydrolysate as an active agent for strengthening hair and improving hair health. The disclosure also concerns the use of this novel active agent for making a derma-pharmaceutical composition intended to stimulate hair growth or to prevent hair loss as part of a preventive or curative treatment for hair loss related to a pathological condition.

The disclosure further relates to a cosmetic treatment method designed to stimulate hair growth or prevent hair loss and to prevent external aggressions which affect hair, in which a composition containing the active agent is applied topically to the treatment area.

The disclosure further relates to a cosmetic treatment method intended to prevent or counteract external aggressions.

Hair growth and hair renewal are primarily determined by the activity of hair follicles and their matrix environment.

The hair follicle is a complex independent skin appendage which comprises six major compartments, some of dermal origin (conjunctive tissue sheath and dermal papilla) and some of epithelial origin (internal and external epithelial root sheathes, hair shaft and sebaceous stem). At the base of the follicle is found the highly vascularized matrix, which is the origin of the three concentric layers of the hair. The hair consists of differentiated epithelial cells essentially containing keratins, which are in turn organized according to very stable protein superstructures. The organization and strength of the hair shaft and hair are determined by the activity and health of the follicle.

The hair follicle is renewed according to a cycle consisting of three phases: the anagen phase, the catagen phase, and the telogen phase.

The anagen phase (growth phase) lasts between one and ten years and is characterized by a constant lengthening of the hair. At the beginning of each anagen phase, development of the perifollicular microvascular network is observed. Perifollicular microcirculation therefore plays a fundamental role in the hair growth process by providing factors and nutrients needed for follicle growth.

The catagen phase which follows only lasts a few weeks. During this phase, the blood capillaries collapse and disappear. The follicle atrophies and withdraws to the surface, with the noteworthy exception of the dermal papilla, which will be the key element of future regeneration.

The terminal or telogen phase, which lasts a few months, is a rest phase for the follicle, after which the hair ends up dropping. At the end of this rest period, a new follicle is regenerated and a new cycle begins.

Furthermore, it has been well documented that the differentiation mechanisms of keratinocytes of the epidermis and hair follicle are substantially different. For instance, it is known that hair shaft keratins are a family of keratins separate from that expressed in the epidermis (Langbein et al., 2001, J. Bioi. Chem. 276); for instance, keratin K6irs (Porter et al., 2001, Br. J. Dermatol. 145: 558-568) is expressed in the internal sheath of the hair follicle, but not in the epidermis, whereas the epidermal differentiation markers, such as keratins K1 and K10, are not expressed in the hair follicle (Lenoir et al., 1988, Dev. Biol. 130: 610-620).

Natural dropping or loss of hair can be estimated at about one hundred hairs, on average, per day for a normal physiological condition. This ongoing renewal process can be disrupted by numerous intrinsic and extrinsic factors resulting in substantial hair loss, be it temporary or not, which come under the general term of alopecia. For instance, microcirculation disturbances have been observed in alopecic skin. At the same time, a kind of perifollicular fibrosis takes root in alopecic areas, the follicles shrink from one cycle to the next, and vascularization of the bulbs progressively dwindles.

In addition, the ongoing physiological hair renewal process is subject to aging. While the most visible sign of hair aging is graying, the quality of the hair follicle's biological environment is also affected. Among the manifestations of hair aging we find diminished synthesis of the extracellular matrix proteins (collagen, laminin, fibronectin), resulting in a loss of elasticity and tonus of the subcutaneous tissues. There is also a drop in the coherence and organization of hair follicles, a decrease in the duration of the anagen phase, and a lengthening of the duration of the telogen phase (Courtois et al., 1995, Br. J. dermatol., 132: 86-93). In effect, the hair loses its elasticity and becomes thinner and therefore more fragile. Considering the scalp as a whole, aging is evidenced by a drop in capillary density and by a gradual decrease in the diameter of the follicles, giving the hair a thinner, more sparse appearance (Pelfini, C. et al., J. Med. Esth. Et Chir. Derm. 1987; Birch M P et al. Br. J. Dermatol 2001; 144: 297-304).

Independently of intrinsic aging, alterations of the hair or hair follicle may occur as a result of external aggressions. Indeed, although hair is remarkably stable, certain external factors such as the sun, which causes photo-aging, free radicals, pollution, or certain inappropriate treatments, can lead to premature damage to the structure of hair and follicle depletion.

The expression "external aggression" is understood to mean aggressions which the environment can produce. As an example, let us mention aggressions such as pollution, ultraviolet light, or irritating products such as excessively detersive surfactants, dyes and bleaches, excessively frequent permanents or straightening, mechanical aggressions such as rubbing by clothing, hair styling causing repeated stretching, overly intense brushing, teasing, and blow-drying with air that is too hot. Pollution is understood as both "external" pollution due, for example, to diesel particles, ozone, or heavy metals, and "internal" pollution, which may be due, for instance, to solvent emissions from paints, glues, or wallpaper (such as toluene, styrene, xylene, or benzaldehyde), or cigarette smoke. These external aggressions lead to an alteration of the external hair structure and the hair's mechanical properties, but can also affect the hair follicle and cause premature aging.

The cosmetic or pharmaceutical industry is always looking for compositions which can eliminate or reduce hair loss or stimulate hair growth. Worth mentioning is the known molecule 2,4-diamino-6-piperidinopyrimidine-3-oxide or "Minoxidil" (U.S. Pat. Nos. 4,139,619 and 4,596,812). A known compound for maintaining perifollicular vascularization is 4-verapamil, described as being active in the treatment of hair loss, particularly through their effects on microcirculation (JP 88/062680).

Furthermore, there are other patents describing the use of topical vasodilators intended to stimulate hair growth by acting on the microcirculation of the scalp (EP 327 263). Another patent document by Shiseido (JP 07316023) also describes the use of arginine and its derivatives in the treatment of alopecia. However, some available products have side effects, such as in the case of Minoxidil, or have a limited effectiveness that lasts only as long as the treatment. Consequently, there is a need for a new, physiologically acceptable composition for promoting hair growth and/or reducing hair loss which acts quickly and is effective over the long term.

Yeast peptide extracts have previously been described for their hair fiber hydration properties for use in hair conditioner compositions (EP0695801).

In addition, yeast peptide extracts have previously been described for their effects on skin (FR 2904 552, FR 2887 772). The inventors have now shown that such yeast peptide hydrolysates had an action in strengthening the hair follicle structure and improving hair health. In particular, it has been demonstrated that the peptide hydrolysate, when applied to hair, increases differentiation of the epithelial cells in the external sheath of the follicle, improves vascularization of the follicle, and increases the expression of extracellular matrix proteins.

The first subject matter of the disclosure is the cosmetic use of a composition comprising at least one yeast (*Saccharomyces cerevisiae*) peptide hydrolysate as an active agent for strengthening hair and improving hair health.

The human keratin fibers to which the disclosure applies are hair, eyebrows, eyelashes, facial hair, pubic hair, and nails. More specifically, the disclosure applies to human hair and/or eyelashes.

A "peptide hydrolysate" is understood as a mixture of compounds consisting for the most part of peptides or oligopeptides. According to the disclosure, the terms "peptide hydrolysate" and "active agent" will be used indifferently.

The phrase "active agent capable of strengthening hair and improving hair health" refers to any peptide hydrolysate coming from yeast which is capable of increasing the expression of keratins K14 and K17, increasing the expression of extracellular matrix proteins such as collagen I, and increasing the expression of basal plate proteins such as collagen IV.

It is also understood that the active agent is capable of increasing the expression of proteins present in the wall of blood vessels in the follicle, such as protein CD34 and collagen IV.

The active agent according to the disclosure can be made by extraction of yeast proteins followed by controlled hydrolysis which releases compounds having a peptide nature.

"Compounds having a peptide nature" are understood as the protein fragments and peptides present in the peptide hydrolysate of the disclosure.

The use of peptide hydrolysates, and particularly low-molecular-weight peptide hydrolysates, offers numerous benefits in cosmetics. In addition to generating compounds having a peptide nature which did not exist in the initial protein mixture, hydrolysis and purification make it possible to obtain more stable mixtures which are more easily standardized and do not trigger allergic reactions in derma-cosmetics.

The hydrolysate from the yeast genus *Saccharomyces* must be understood as a yeast hydrolysate belonging to the genus *Saccharomyces*. Naturally, the hydrolysate can be prepared from yeast from at least any one of the numerous varieties and species belonging to the genus *Saccharomyces*. According to a preferred embodiment, said active agent comes from the hydrolysis of yeast proteins from the species *Saccharomyces cerevisiae*.

A great number of yeast proteins are likely to contain bioactive peptides in their structure. Controlled hydrolysis makes it possible to bring out these compounds having a peptide nature. It is possible, but not necessary for the purposes of the disclosure, to extract the proteins in question first and to hydrolysate them after, or to first conduct hydrolysis of the raw extract and subsequently to purify the compounds having a peptide nature.

According to a currently preferred method of the disclosure, the yeast hydrolysate is an aqueous extract. An aqueous extract is understood as any combination of compounds soluble in water or in any solvent consisting entirely or partially of water. The extracts of the disclosure are namely purified aqueous extracts. In particular, aqueous solvents may be cited. An aqueous solvent is understood as any solvent consisting entirely or partially of water. Let us mention water itself, glycerol, water-and-alcohol solvents in any proportion, or solvents consisting of water and a compound such as propylene glycol or butylene glycol in any proportion. This hydrolysate can be obtained by dissolving in water, alcohol, or ether, then concentrating the solution by means of evaporation or distillation.

Any extraction or purification method known to a person skilled in the art can be used to prepare the hydrolysate of the disclosure.

For instance, in the first step, the yeasts are cultured in a conventional manner in a medium appropriate for their development, preferably in the presence of lactose. They are collected by centrifugation and then suspended in a buffer solution, preferably a phosphate buffer. In a second step, these cells are disrupted by means of a French press or a ball mill, with most of the insoluble membrane components being eliminated by centrifugation or filtration.

A protein-rich filtrate can then be collected and re-dissolved. A fraction rich in compounds having a peptide nature can then be isolated by precipitation in an alcohol medium or with a saline solution. The soluble components and nucleic acids are thus eliminated. According to a variant of the method for producing the hydrolysate of the disclosure, a dialysis step and a hydrolysis step using a cocktail of proteases can be added to obtain a fraction rich in compounds having a peptide nature.

An additional purification step using a chromatography method can be considered.

According to another method for producing the yeast hydrolysate of the disclosure, the hydrolysis step can be performed directly on the yeasts collected after centrifugation or on the fractions obtained after cell disruption. Filtration and sterilization steps are then performed.

A phase of dilution in water or any mixture containing water is performed, then the dilution is sterilized by ultrafiltration in order to obtain a peptide hydrolysate having a protein concentration of 30% and 70% of the total dry extract weight, with this concentration more specifically being 40% and 50% of the total dry extract weight. The solvents used are physiologically acceptable and conventionally used by a person skilled in the art, and are chosen from glycerol, ethanol, propanediol, butylene glycerol, the dipropylene glycerol, ethoxylated or propoxylated diglycols, cyclic polyhydric alcohols, or any mixture of these solvents.

In this way, the active agent of the disclosure is advantageously dissolved in one or more physiologically acceptable solvents, such as water, glycerol, ethanol, propanediol, butylene glycol, dipropylene glycerol, ethoxylated or propoxylated diglycols, cyclic polyhydric alcohols, or any mixture of these solvents. The diluted active agent is then sterilized by ultrafiltration.

After this dilution step, the active agent can be encapsulated or included in a cosmetic or pharmaceutical vector such as liposomes or any other microcapsule used in the field of cosmetics or adsorbed in powdered organic polymers, mineral substrates such as tales or bentonites.

According to an advantageous embodiment, the active agent is present in the compositions of the disclosure at a concentration of between approximately 0.001% and 5%, and preferably at a concentration of between approximately 0.01% and 1% in relation to the total weight of the final composition.

The compositions which can be used according to the disclosure may be in the form of an aqueous, water-and-alcohol, or oil solution; an oil-in-water emulsion, a water-in-oil emulsion, or multiple emulsions; they may also be in the form of crèmes, suspensions, or powders. These compositions can be more or less fluid and have the appearance of a crème, lotion, salve, serum, ointment, gel, paste, or foam. They may also be in solid form, such as a stick, or be applied to the area requiring treatment in aerosol form. They may be used as a care product and/or as a skin make-up product.

All of these compositions furthermore include any additive customarily used in the field of application under consideration, as well as the additives needed for their formulation, such as co-solvents (ethanol, glycerol, benzyl alcohol, moisturizers, etc.), thickeners, thinners, emulsifiers, antioxidants, dyes, sunscreens, pigments, fillers, preservatives, scents, odor absorbers, essential oils, trace elements, essential fatty acids, surfactants, film-forming polymers, chemical or mineral filters, hydrating agents, or thermal spring water, etc. Let us mention, for example, natural water-soluble polymers such as polysaccharides, polypeptides, cellulose derivatives such as methylcellulose or hydroxypropyl cellulose, or synthetic polymers, poloxamers, carbomers, PVA or PVP, and particularly polymers sold by the company ISP.

In any event, a person skilled in the art will ensure that these additives and their proportions are chosen in such a way as not to harm the desired advantageous properties of the composition of the disclosure. For example, these additives may account for a concentration of between 0.01% and 20% of the total weight of the composition. When the composition of the disclosure is an emulsion, the fatty phase may account for 5% to 80% by weight, and preferably 5% to 50% by weight, in relation to the total weight of the composition. The emulsifiers and co-emulsifiers used in the composition are to be chosen from those conventionally used in the field under consideration. For example, they may be used in a proportion of between 0.3% to 30% by weight, in relation to the total weight of the composition.

The compositions which can be used according to the disclosure may consist of shampoos, conditions, a treatment lotion before or after aggressive hair treatments, a hair crème or gel, a hair restructuring lotion, a mask, etc. The composition may also be in the form of mascara for application to eyelashes, eyebrows, or hair.

Furthermore, the active agent of the disclosure may be used alone or in combination with other active agents.

Advantageously, the compositions which can be used according to the disclosure additionally contain at least one other active agent which protects or improves hair growth and/or health. Let us mention, as non-limiting examples, the following ingredients: vitamins, anti-free radical and anti-UV agents, other plant-based peptide extracts, minoxidil, nicotinic acid esters, anti-inflammatory agents, retinoic acid or its derivatives, retinol, 5-alpha reductase inhibitors, or chemically-synthesized peptide compounds.

The composition which can be used according to the disclosure can be applied by any appropriate means, such as orally, parenterally, or topically, and the formulation of the compositions shall be adapted by a person skilled in the art, particularly for cosmetic or dermatological compositions.

Advantageously, the compositions of the disclosure are intended for topical administration. These compositions must therefore contain a physiologically-acceptable medium, that is, one compatible with the skin and keratinous appendages, and encompassing all cosmetic or dermatological forms.

"Topical application" is understood as the act of applying or spreading the active agent of the disclosure, or a composition containing said agent, to the surface of the skin or a mucous membrane. "Physiologically acceptable" means that the peptide hydrolysate of the disclosure, or a composition containing said hydrolysate, is appropriate for coming into contact with the skin or a mucous membrane without causing toxicity or intolerance reactions.

According to another aspect of the disclosure, the composition containing the yeast (*Saccharomyces cerevisiae*) peptide hydrolysate as the active agent is used to treat alopecia.

Alopecia encompasses a range of hair follicle problems which ultimately result in temporary or permanent, partial or general hair loss. Both men and women can be affected by alopecia, but the areas predominantly affected in men are the temples or forehead, whereas in women there is a diffuse alopecia of the vertex.

The second subject matter of the disclosure is the use of a yeast peptide hydrolysate (*Saccharomyces cerevisiae*) as an active agent for strengthening the hair follicle structures. On the histological level, this action is characterized by increased differentiation of the epithelial cells in the external sheath of the follicle, stimulated vascularization of the hair follicle, and increased density of the extracellular matrix and the basement membrane.

On the molecular level, the action of the yeast (*Saccharomyces cerevisiae*) peptide hydrolysate of the disclosure is characterized by increased expression of keratins K14 and K17.

The action of the yeast (*Saccharomyces cerevisiae*) peptide hydrolysate of the disclosure is also characterized by increased expression of protein CD34 and collagen IV in the wall of hair follicle blood vessels.

The action of the yeast (*Saccharomyces cerevisiae*) peptide hydrolysate of the disclosure is further characterized by increased expression of collagen I in the extracellular matrix and increased expression of collagen IV in the basement membrane of the hair follicle.

The third subject matter of the disclosure refers to a cosmetic treatment method intended to prevent or counteract external aggressions against hair, characterized in that the composition of the disclosure is applied topically to the area being treated.

The fourth subject matter of the disclosure refers to a cosmetic treatment method intended to restore and/or stimulate hair growth or counteract hair loss, characterized in that the composition of the disclosure is applied topically to the area being treated.

According to a special embodiment, the disclosure refers to a cosmetic treatment method intended to restore and/or stimulate eyelash growth or counteract eyelash loss, characterized in that the composition of the disclosure is applied topically to the area being treated The disclosure also refers to the use of a yeast (*Saccharomyces cerevisiae*) peptide hydrolysate as an active agent capable of strengthening and protecting the hair follicle for making a derma-pharmaceutical composition intended to stimulate hair growth or to counteract hair loss as part of a preventive or curative treatment for hair loss related to a pathological condition. Of the pathological conditions frequently responsible for hair loss, let us mention alopecia areata, the side effects of drug treatments, and certain infections or inflammations of the scalp (psoriasis, seborrheic dermatitis, etc.).

According to this embodiment of the disclosure, the compositions are appropriate for oral administration for pharmaceutical use. For instance, the compositions can be in the form of tablets, capsules, gelcaps, chewing paste, powders to be ingested as is or to be mixed extemporaneously with a liquid, syrup, or gel, and any other form known to a person skilled in the art. These compositions furthermore include any additive customarily used in the field of application under consideration, as well as any additives required for their formulation, such as solvents, thickeners, thinners, antioxidants, preservatives, other pharmaceutical active agents, essential oils, vitamins, essential fatty acids, etc.

The disclosure furthermore refers to a cosmetic treatment method intended to prevent or counteract the signs of aging and photo-aging of the hair, characterized in that the composition of the disclosure is applied topically to the area being treated.

The disclosure furthermore refers to a cosmetic treatment method intended to stimulate nail growth, characterized in that the composition of the disclosure is applied topically to the area being treated.

Particular embodiments of this cosmetic treatment method also arise from the foregoing description. Other advantages and features of the disclosure will become more readily apparent upon reading the examples, which are given solely for non-limiting, illustration purposes.

BRIEF DESCRIPTION OF THE FIGURES

FIG. 2 is a statement of formulation of the active ingredient composition of Example 7

FIG. 3 illustrates Examples of the typical morphological aspects of hair fibers observed in Example 7.

FIG. 7 provides a schematic of how a hair follicle is biopsied for responses to the active ingredient composition.

FIG. 8 is a photograph showing the increase in outer root sheath as a result of treatment with the active composition of the disclosure, in particular with respect to Keratin 14 expression.

FIG. 11 are pictures showing increases in trichohyalin and K 71 increases after treatment of hair with the active ingredient composition of the disclosure.

FIG. 12 shows pictures of Collagen I and Collagen IV increases after treatment of hair with the active ingredient composition of the disclosure.

FIG. 13 shows a summary of the effects of treatment of the active composition of the disclosure FIG. 14 shows a table of a conditioning spray milk containing the active ingredient composition of the disclosure.

FIG. 15 shows a table of an active ingredient-containing hair and scalp nourisher cream.

FIG. 16 shows the activity of the proteins of the active ingredient composition of the disclosure as measured by a K 14 Marker.

FIG. 17 shows anti-hair fall clinical study conditions and protocols according to Example 7 of the disclosure.

FIG. 18 shows a table describing the formulation of a conditioning milk spray of Example 7 of the disclosure.

FIG. 19 shows a table of the formulation of a placebo used in Example 7 of the disclosure.

FIG. 20 shows a study design schematic of Example 7 of the disclosure.

FIG. 21 shows a study design schematic according to Example 7 of the disclosure.

FIG. 23 shows a schematic of the methodology of Example 7 of the disclosure.

FIG. 24 shows a schematic and protocol for a anti-hair fall clinical study according to Example 7 of the disclosure.

FIG. 26 shows long-term study graphs of the Anagen to Telogen ratio after 30, 60, and 90 days according to Example 7 of the disclosure FIG. 27 shows a summary of Anagen to Telogen ratios according to Example 7 of the present disclosure.

FIG. 33 provides interview comments from participants of Example 7 of the disclosure.

FIG. 34 provides a table of conclusions according to Example 7 of the disclosure.

EXAMPLE 1

Figure 1:
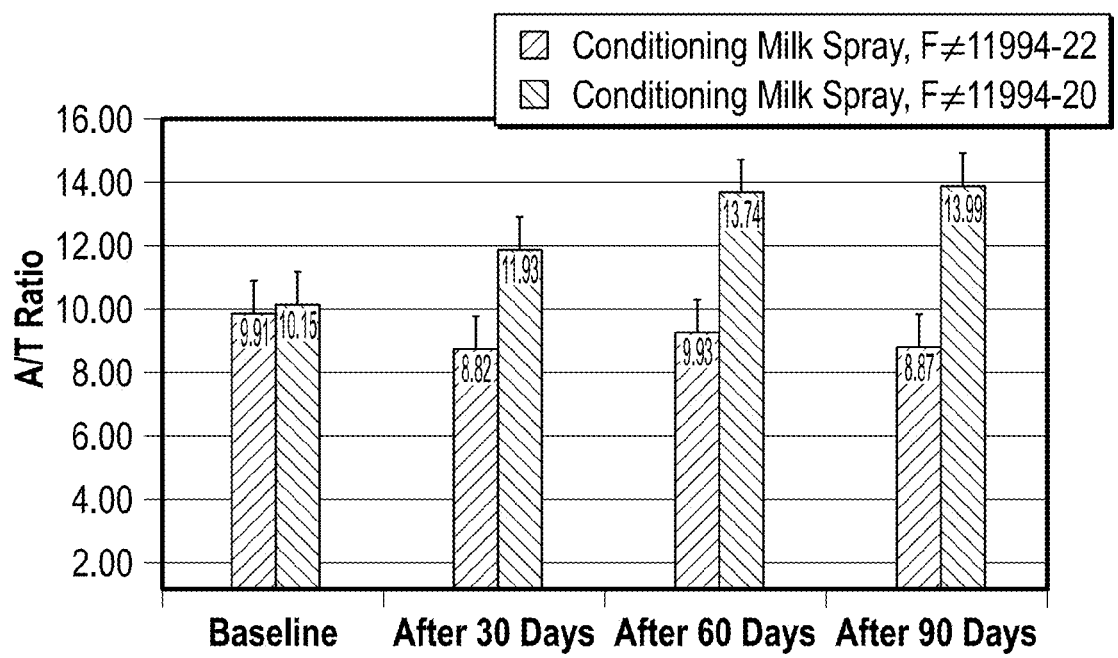
FIG. 1 is a graph showing mean values of Anagen to Telogen ratios over a study as described in Example 7.
Figure 4:
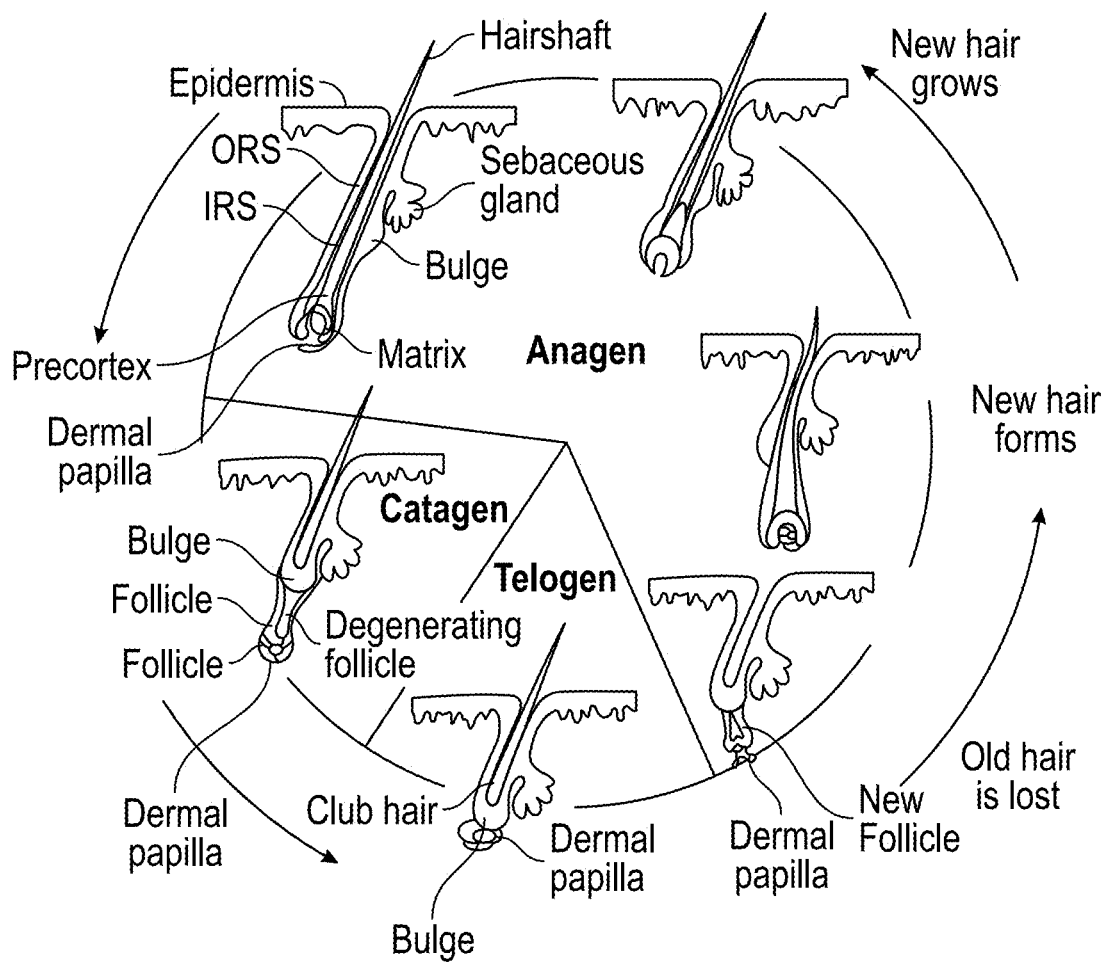
FIG. 4 provides a schematic representation of hair life.
Figures 5, 6:
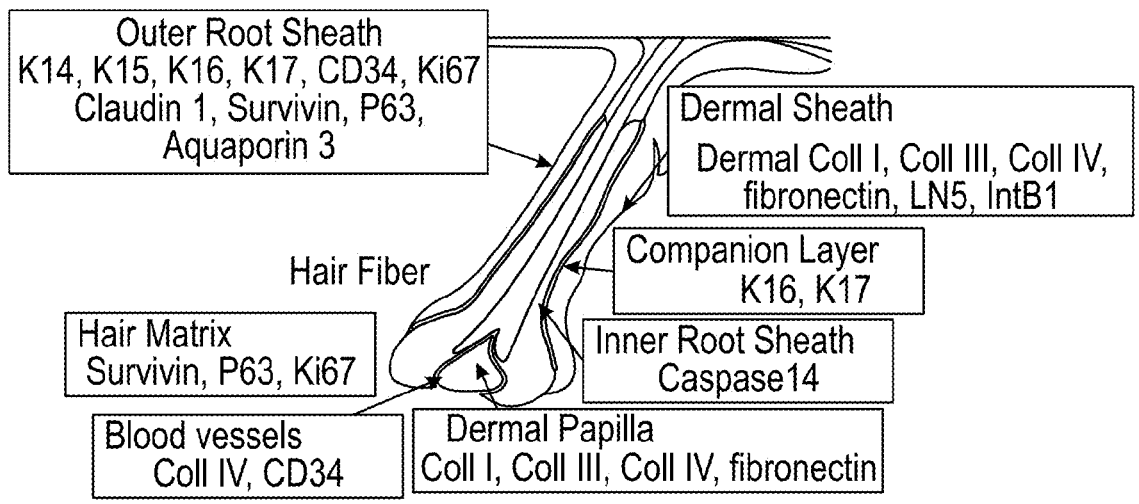
FIG. 5 shows a mapping of different biochemical aspects of hair follicles.
FIG. 6 provides a description of markers that are influenced by the active ingredient of the composition of the disclosure.
Figure 9:
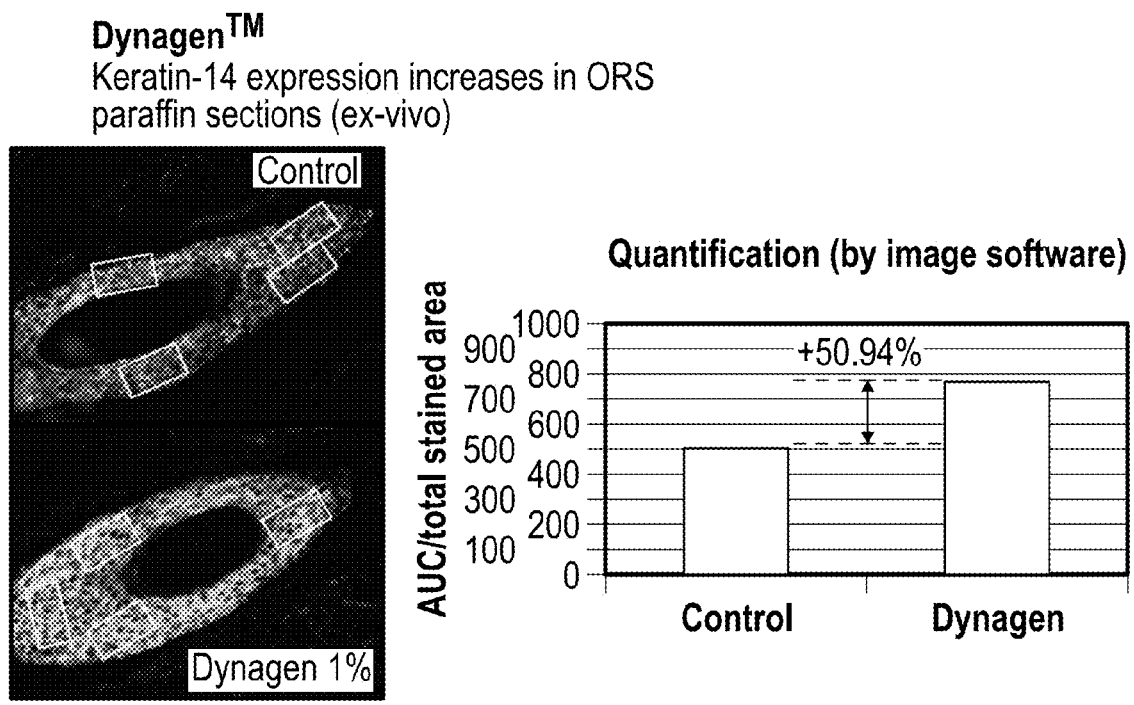
FIG. 9 shows a graph and picture quantifying the increasing Keratin 14 expression by treatment of the composition of the disclosure.
Figure 10:
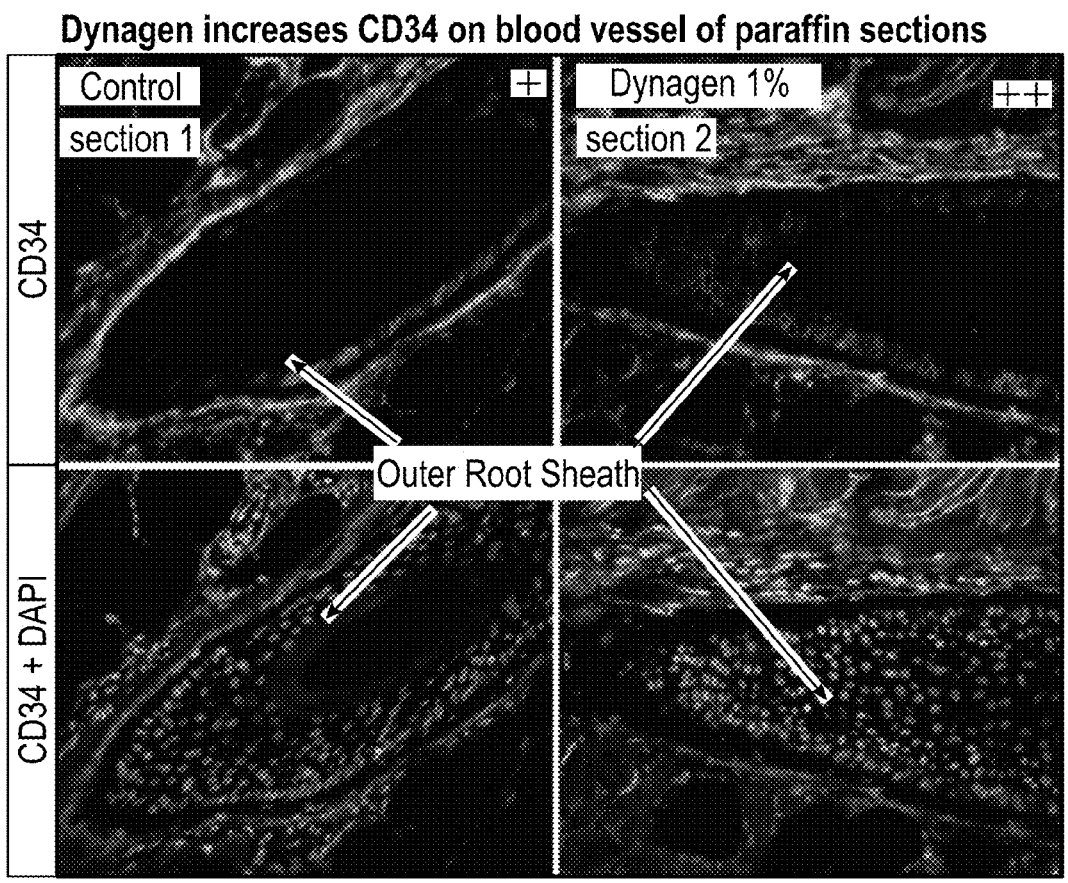
FIG. 10 is a picture showing CD34 increases on blood vessels after treatment affairs with the active ingredient composition of the disclosure.
Figure 22:
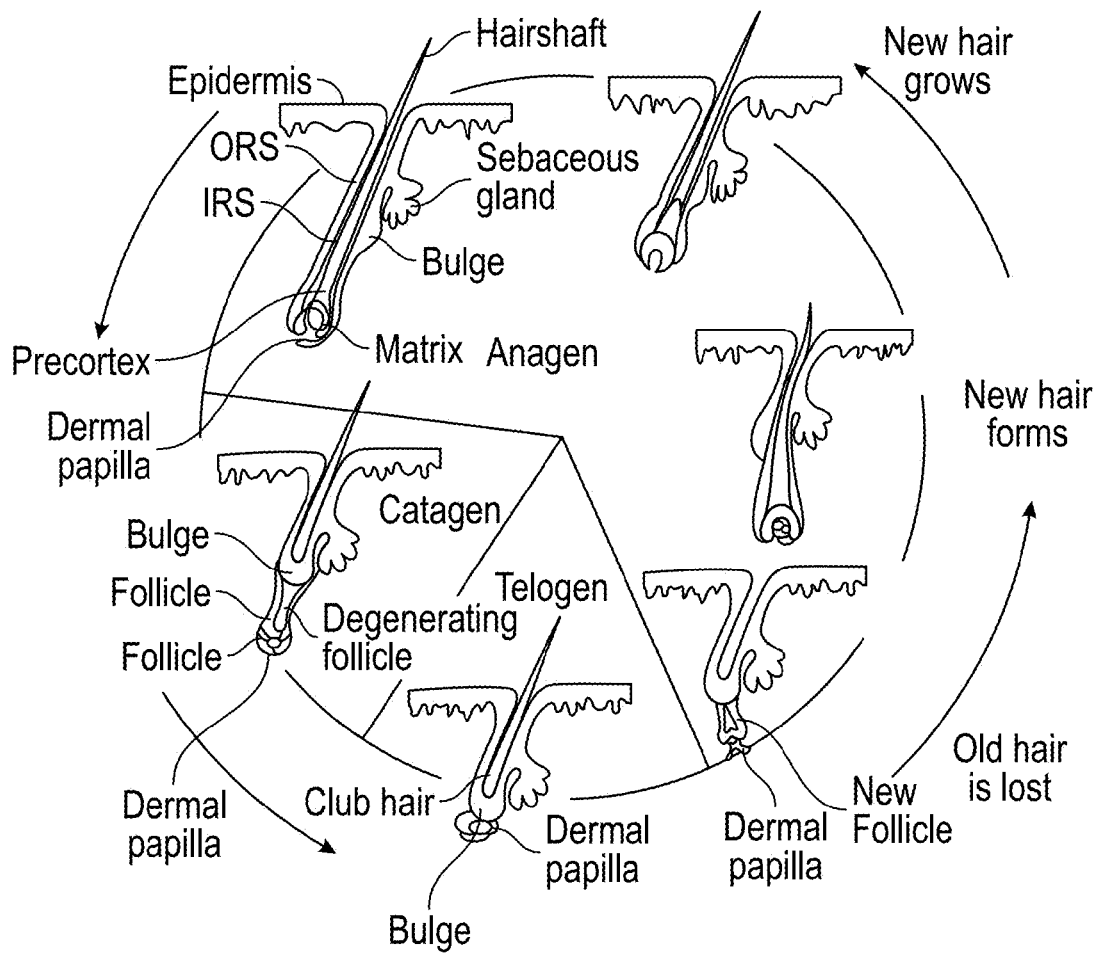
FIG. 22 describes the methodology for measuring Anagen to Telogen ratios in Example 7 of the disclosure.
Figure 25:
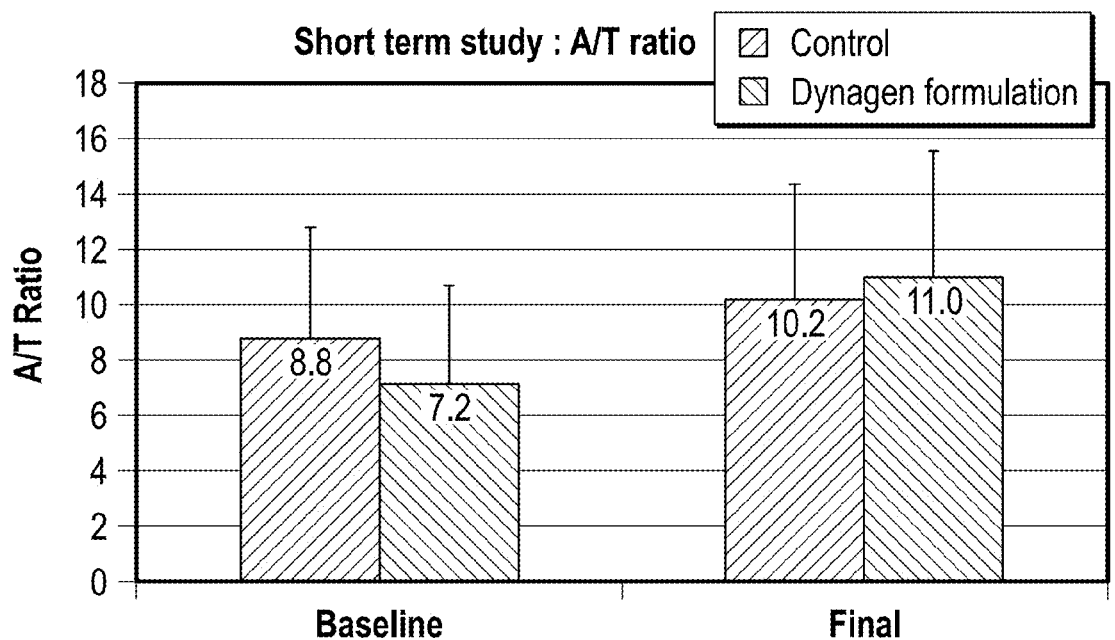
FIG. 25 shows at Anagen to Telogen ratios after 30 days according to Example 7 of the disclosure.
Figure 28:
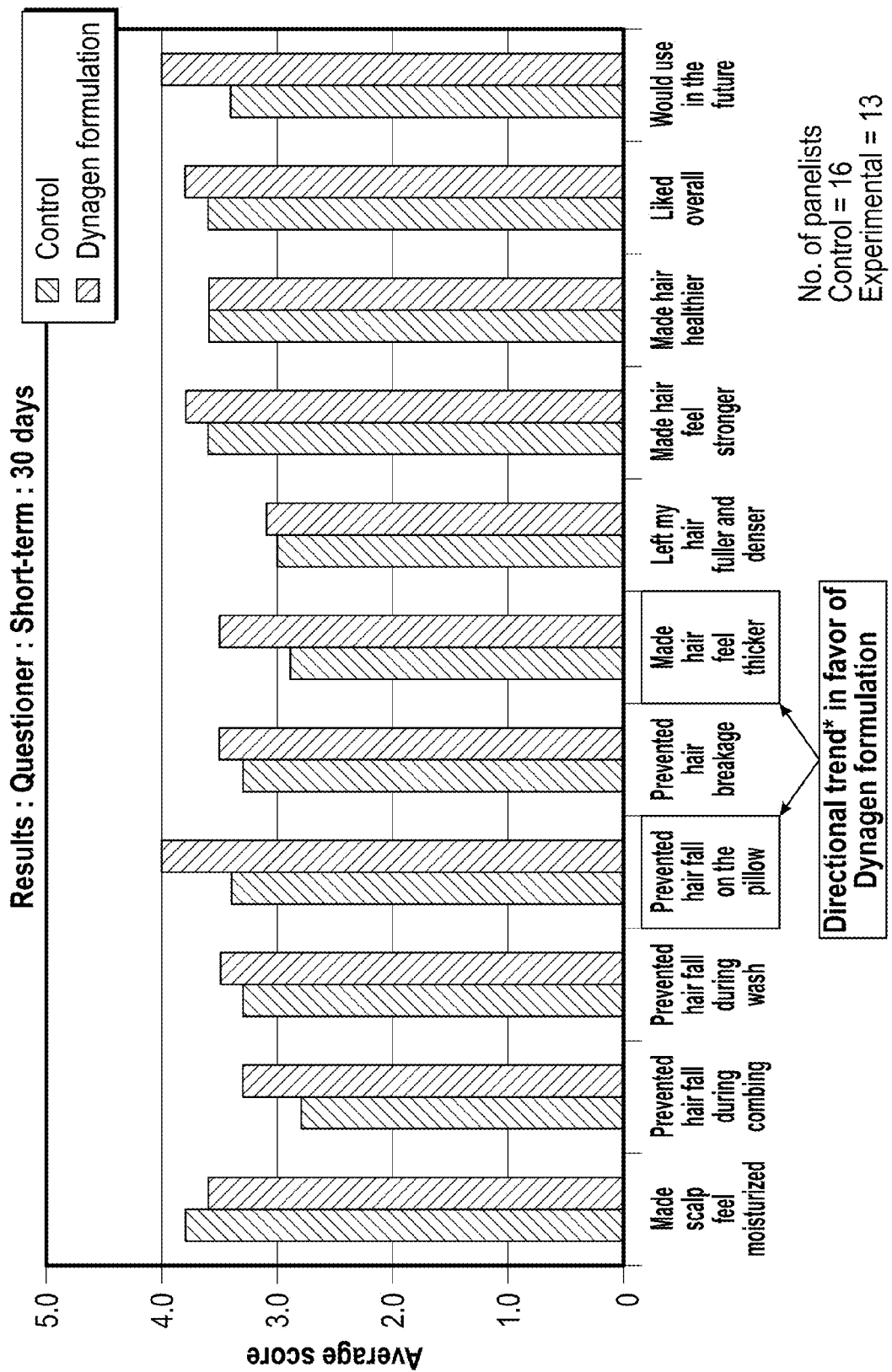
FIG. 28 shows results of questionnaires after 30 days according to Example 7 the present disclosure.
Figure 29:
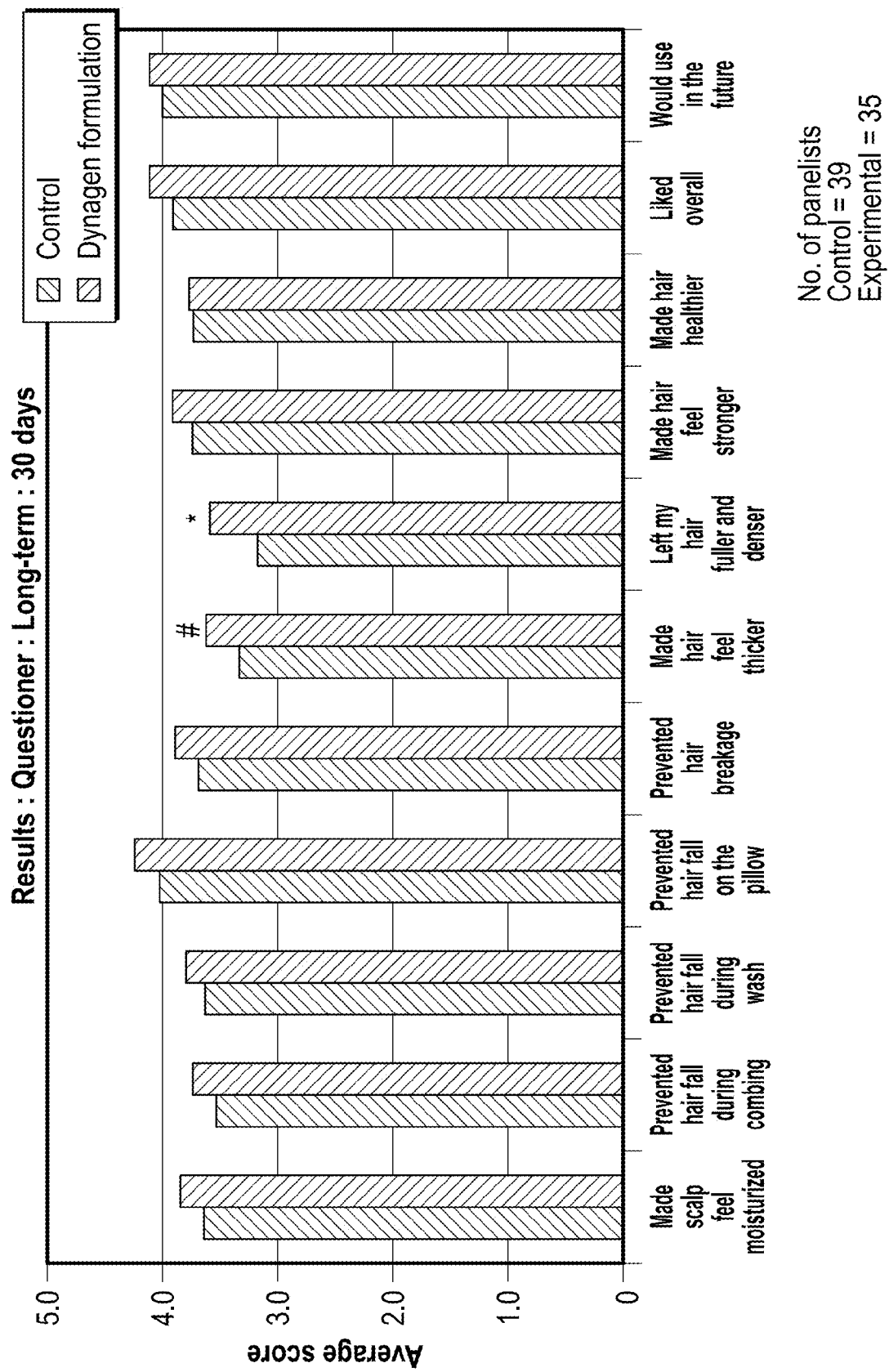
FIG. 29 shows long-term results from a questionnaire provided to participants in Example 7 of the disclosure.
Figure 30:
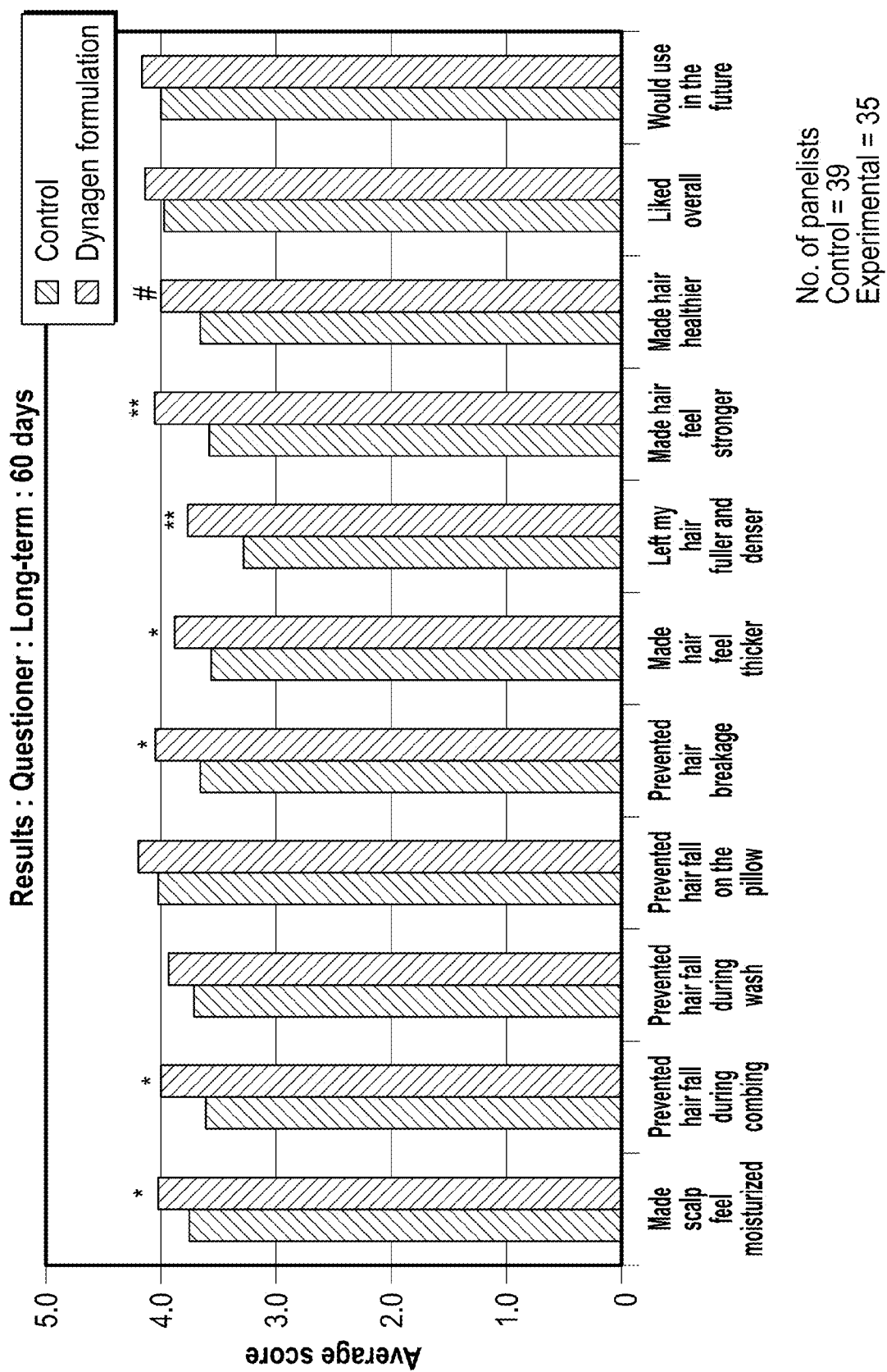
FIG. 30 shows results of a questionnaire after 60 days according to Example 7 of the present disclosure.
Figure 31:
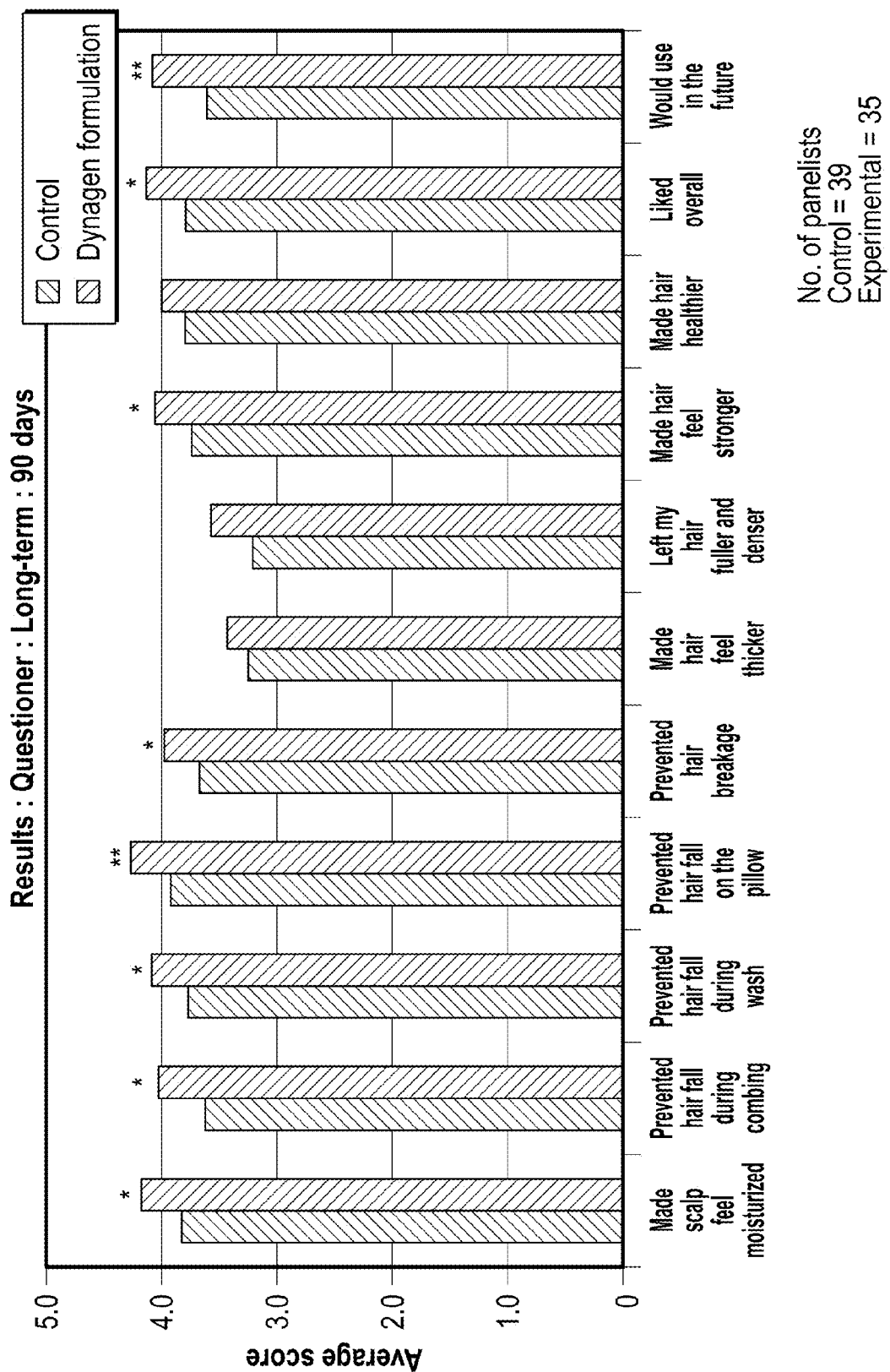
FIG. 31 shows the results of a long-term treatment using the composition of the disclosure after 90 days according to Example 7 of the present disclosure.
Figure 32:
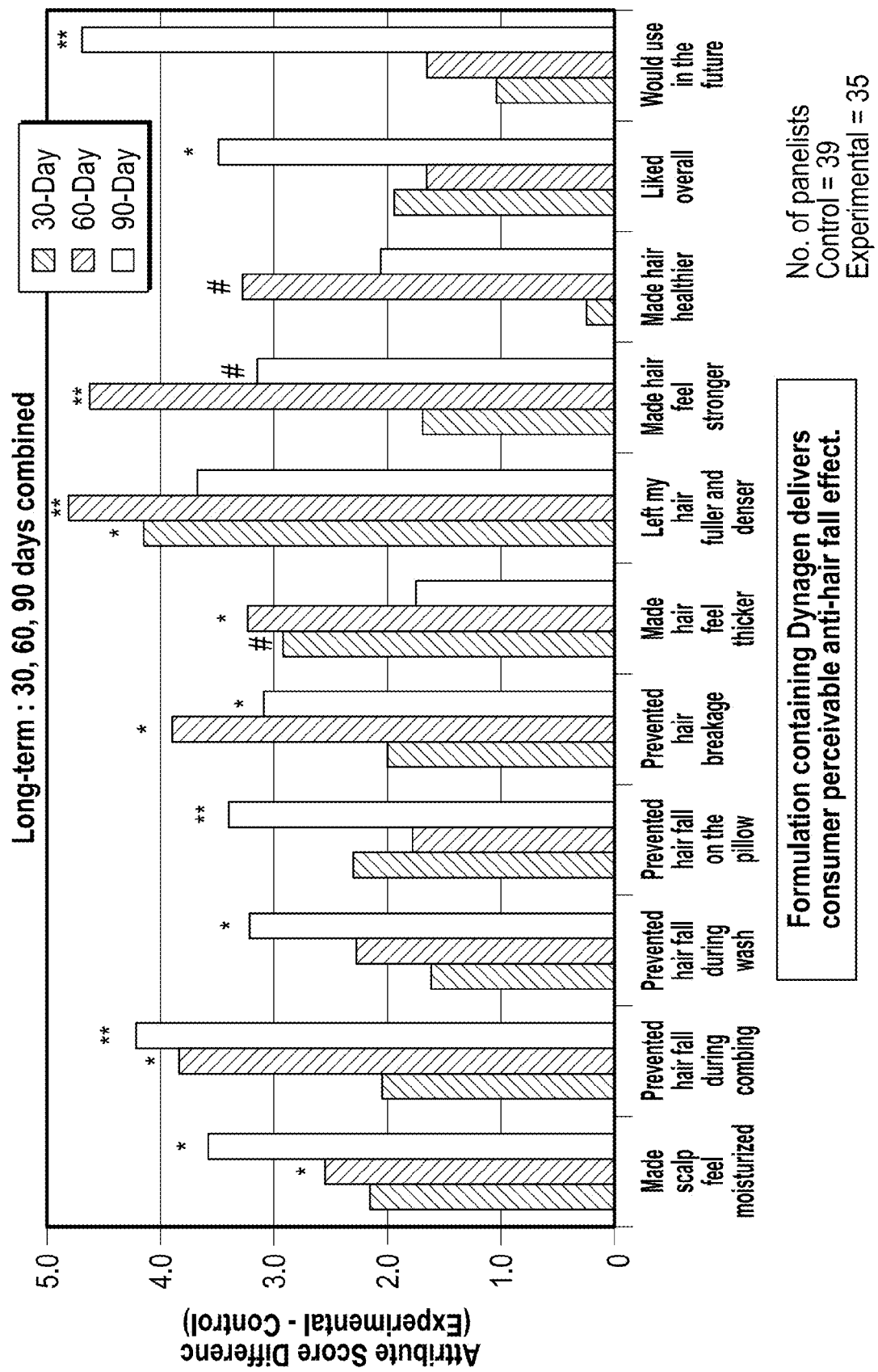
FIG. 32 shows a graph of participant responses to the questionnaire after 30, 60, and 90 days according to Example 7 of the present disclosure.

Preparation of a Yeast (*Saccharomyces cerevisiae*) Peptide Hydrolysate

The active agent is obtained from a yeast extract from the species *Saccharomyces cerevisiae*. The yeasts are cultured in a medium suitable for their development, then centrifuged to recover a biomass.

The biomass is then milled in a ball mill. Next, the ground material is re-dissolved in water at a concentration of 100 grams per liter, before enzymatic hydrolysis at between 40% and 60° C. for 6 hours. After hydrolysis, the extract is centrifuged and then diluted in a water-glycerol mixture. The extract is then filtered before sterilization.

A hydrolysate containing a quantity of protein and peptide compounds accounting for approximately 30% to 70% of the total weight of the dry extract is obtained, with this quantity especially being between 40% and 50% of the total weight of the dry extract.

A determination of the amino acid composition of the active agent of the disclosure was also performed. After assaying the proteins and peptides using the Lowry method, acid hydrolysis was performed to reduce all the peptides to the state of free amino acids. An example of the amino acid composition of the hydrolysate is given in the following table. The values are expressed in percentage of amino acids per 100 g of proteins.

| Amino acids | % |
|---|---|
| Alanine | 7.4 |
| Aspartic acid | 12.0 |
| Arginine | 4.6 |
| Glutamic acid | 15.6 |
| Glycine | 5.5 |
| Histidine | 2.8 |
| Isoleucine | 4.6 |
| Leucine | 9.2 |
| Lysine | 8.3 |
| Phenylalanine | 5.5 |
| Proline | 4.6 |
| Serine | 6.5 |
| Threonine | 5.5 |
| Tyrosine | 4.6 |
| Valine | 6.5 |
| Tryptophan | ND |

EXAMPLE 2

Demonstration of Stimulated Differentiation of the Epithelial Cells in the External Sheath of the Hair by the Hydrolysate of Example 1

The purpose of this study is to determine the influence of the hydrolysate of example 1 on the differentiation of epithelial cells in the external sheath of the hair. To do this, keratinocyte differentiation markers were studied. Keratin K14 is an early differentiation marker expressed in the proliferative compartment of the external epithelial root sheath of the hair follicle. Keratin K17 is late differentiation marker closely associated with the strength of the hair shaft.

Protocol: Skin biopsies measuring 6 mm in diameter, coming from face lifts and containing hair follicles, were cultured on inserts in William's E medium and then treated for 48 hours with the hydrolysate of example 1 at 1%. Untreated controls were also made. At the end of the experiment, the biopsies were placed in cassettes and dipped into a 10% mixture of formaldehyde for 2 hours in an automated instrument (VIP). The paraffin coating was prepared by a series of alcohol baths (with increasing concentrations and times), followed by 2 xylene baths and lastly a paraffin bath. The total duration of this series of operations was about 12 hours. The biopsies included in paraffin were then cut to 4 11 m by a microtome and placed on slides. The slides are deparaffinized, rehydrated, and then subjected to immunolabeling with a monoclonal antibody directed against keratin K14 (Abeam) or a monoclonal antibody directed against keratin K17 (Abeam), then a second appropriate antibody coupled to a fluorescent marker. The skin slices are then examined with an Bpi-fluorescence microscope (Nikon Eclipse E 80i microscope).

Results: A much more intense fluorescence of the external epithelial root sheath cells is observed in the hair follicle slices treated with the hydrolysate according to example 1 and marked for keratin K14 or keratin K17, compared to the untreated control.

Using fluorescence quantification software, a 44% increase for keratin K14 and a 44% increase for keratin K17 can be measured.

Conclusions: The hydrolysate of example 1 increases keratinocyte differentiation, particularly for keratin K17 which is closely associated with hair shaft strength. The hydrolysate of example 1 increases the cohesion of the epithelial root sheath and improves the conformation of the internal epithelial root sheath.

On the whole, this study demonstrates that the active agent of the disclosure strengthens hair structure.

EXAMPLE 3

Demonstration of the Stimulating Effect of the Hydrolysate of Example 1 on Hair Follicle Vascularization The purpose of this study is to determine the influence of the hydrolysate of example 1 on the hair follicle blood vessels. To do this, the expression of blood vessel wall markers was studied.

Protocol: The cultures and paraffin inclusions were made according to the same protocol as example 2. The slides were deparaffinized, rehydrated, and then subjected to an unmasking step and then immunolabeling with a monoclonal antibody directed against collagen IV (Chemicon) or against protein CD34 (Novocastra), then an adapted secondary antibody coupled to a fluorescent marker. The skin slices were then examined with an Bpi-fluorescence microscope (Nikon Eclipse E 80i microscope).

Results: A more intense fluorescence of the basal plate and the blood vessel wall is observed in the hair follicle slices treated with the hydrolysate of example 1, in which the collagen IV was immunolabeled, compared to the untreated control. Using fluorescence quantification software, a 144% increase can be measured.

A more intense fluorescence of the blood vessel wall and the conjunctive tissue sheath is observed in the hair follicle slices treated with the hydrolysate of example 1, in which protein CD34 was immunolabeled, compared to the untreated control.

Conclusions: The hydrolysate of example 1 improves the blood circulation of the follicle, which has the result of increasing the supply of nutrients and thus improving hair health.

In addition, the hydrolysate of example 1 improves the hair follicle structures.

EXAMPLE 4

Demonstrating the Strengthening of Matrix Structures by the Hydrolysate of Example 1

The purpose of this study is to determine the influence of the hydrolysate of example 1 on the extracellular matrix and the dermal papilla of the follicle. To do this, the expression of one of the primary proteins of the matrix was studied.

Protocol: The cultures and paraffin inclusions were made according to the same protocol as example 2. The slides were deparaffinized, rehydrated, and then subjected to an unmasking step and then immunolabeling with a monoclonal antibody directed against collagen I (Tebu-Rockland), then an adapted secondary antibody coupled to a fluorescent marker. The skin slices were then examined with an Bpi-fluorescence microscope (Nikon Eclipse E 80i microscope).

Results: A more intense fluorescence of the conductive tissue sheath and the dermal papilla is observed in the hair follicle slices treated with the hydrolysate of example 1, in which the collagen I was immunolabeled, compared to the untreated control.

Conclusions: The hydrolysate of example 1 strengthens the dermal part surrounding the follicle and thus provides better cohesion and better protection of the hair follicle structure.

EXAMPLE 5

Preparation of Compositions

1—Nourishing Treatment for Hair and Scalp

Apply the product to the wet scalp. Massage to spread the product uniformly. Strengthens hair while making it smooth and easy to style.

| INCI Name | Trade name | Formulation 1 % by weight | 2 % by weight | Supplier |
|---|---|---|---|---|
| Phase A | | | | |
| Deionized Water | — | Q.S. | Q.S. | |
| Aminomethyl Propanol | AMP-95 ™ | 0.05 | 0.05 | |
| Acrylic Acid/VP Crosspolymer | ULTRATHIX ™ P-100 | 0.85 | 0.85 | ISP |
| Phase B | | | | |
| Glycerol Dilaurate | EMULSYN ™ GDL | 0.50 | 0.50 | ISP |
| Jojoba Seed Oil | — | 2.00 | 2.00 | Lipo |
| Cetearyl Alcohols | — | 2.00 | 2.00 | Rita |
| Phase C | | | | |
| Cyclopentasiloxane | SITEC ™ CM040 | 0.50 | 1.00 | ISP |
| Phase D | | | | |
| VP/DMAPA Acrylates Copolymer | STYLEZE ® CC-10 | 3.00 | 3.00 | ISP |
| Water | | 20.00 | 20.00 | |
| Aminomethyl Propanol | | 0.37 | 0.37 | |
| Phase E | | | | |
| Diazolidinyl Urea (and) Methylparaben (and) Propylene Glycol | GERMABEN ® M | 0.75 | 0.75 | ISP |
| Hydrolysate of Example 1 | | 0.5 | 1.00 | ISP |
| Total | | 100.00 | 100.00 | |

Put the water and AMP-95 (Aminomethyl Propanol) in a container with stirring. Add the ULTRATHIX™ P-100 (Acrylic Acid/VP Crosspolymer) to the water with vigorous stirring and keep stirring for 30 minutes. Heat phase A to 65° C. Heat the phase B ingredients to 65° C. then mix them. Add to phase B and mix carefully. Cool to 35° C. Add phase C to the primary mixture and mix until a uniform appearance is obtained.

Separately, mix the ingredients of phase D until a uniform appearance is obtained. Add the GERMABEN® M (Diazolidinyl Urea (and) Methylparaben (and) Propylene Glycol) (Phase E) and mix until a uniform appearance is obtained. Add the hydrolysate of example 1 and stir until a uniform appearance is obtained.

2—Hair Growth Serum

Apply the product to the wet scalp. Massage to spread the product uniformly. Promotes hair growth or regrowth and makes hair stronger.

| INCI Name | Trade name | Formulation 1 % by weight | 2 % by weight | Supplier |
|---|---|---|---|---|
| Water | | Q.S. | Q.S. | |
| Hydroxyethylcellulose | NATROSOL ® 250HHR | 0.35 | 0.50 | Hercules/ Aqualon |
| Disodium EDTA | DISSOLVINE ™ NA-2S | 0.05 | 0.05 | Akzo Nobel |
| VP/DMAPA Acrylates Copolymer | STYLEZE ® CC-10 | 5.00 | 5.00 | ISP |
| Quaternium-26 | CERAPHYL ® 65 | 1.00 | 1.00 | ISP |
| Panthenol | RITAPAN ™ DL | 0.15 | 0.15 | RITA |
| Propylene Glycol (and) Diazolidinyl Urea (and) Iodopropynyl Butylcarbamate | Liquid GERMALL ® Plus | 0.50 | 0.50 | ISP |
| Hydrolysate of example 1 | | 1.00 | 1.00 | ISP |
| Total | | 100.00 | 100.00 | |

Disperse the NATROSOL™ 250HHR (Hydroxyethylcellulose) and the Disodium EDTA in the water with stirring. Heat to 50-60° C. and stir until a uniform appearance is obtained. Add the STYLEZEe® Cc-10 (VP/DMAPA Acrylates Copolymer) and stir until a uniform appearance is obtained. Allow to cool to ambient temperature and add the ingredients in the order listed while stirring until a uniform appearance is obtained after each addition.

3—Non-Aerosol Treatment Foam

Apply the product to the wet scalp. Massage to spread the product uniformly. Strengthens hair vitality and health and promotes a long styling hold, especially in a damp atmosphere.

| INCI Name | Trade name | Formulation 1 % by weight | 2 % by weight | Supplier |
|---|---|---|---|---|
| Water | | Q.S. | Q.S. | |
| PEG-45M | POLYOX ™ N-750 | 0.075 | 0.075 | Dow |
| Polyquaternium-55 (20%) | STYLEZE ® W | 5.00 | 5.00 | ISP |

-continued

| | | Formulation | | |
|---|---|---|---|---|
| | | 1 | 2 | |
| INCI Name | Trade name | % by weight | % by weight | Supplier |
| Propylene Glycol (and) Diazolidinyl Urea (and) Iodo-propynyl Butyl-carbamate | Liquid GERMALL ® Plus | 0.50 | 0.50 | ISP |
| PEG/PPG-25/25 Dimethicone | SITEC ™ DMC 6031 | 1.00 | — | ISP |
| Palmitamidopropyl-trimonium Chloride | VARISOFT ™ PATC | — | 0.80 | Degussa |
| | Hydrolysate of example 1 | 1.00 | 1.00 | ISP |
| Total | | 100.00 | 100.00 | |

Put water in a suitable container and stir vigorously to create a vortex. Disperse the POLYOX™ N-750 (PEG-45M) into the vortex and stir until completely dissolved. Add the STYLEZE® W-20 and stir until a uniform appearance is obtained. Next, add the ingredients in the order listed while stirring until a uniform appearance is obtained after each addition.

Embodiments

Cosmetic use of a composition comprising at least one yeast (*Saccharomyces cerevisiae*) peptide hydrolysate, obtained by cells disruption and elimination of most of the insoluble membrane components, as an active agent for strengthening hair and improving hair health.

A use according to embodiment 1, characterized in that the peptide hydrolysate has a protein concentration of 30% to 70% of the total weight of the dry extract, and more specifically 40% to 50% of the total weight of the dry extract.

A use according to one of the foregoing embodiments, characterized in that the peptide hydrolysate is dissolved in one or more physiologically acceptable solvents, such as water, glycerol, ethanol, propanediol, butylene glycol, dipropylene glycerol, ethoxylated or propoxylated diglycols, cyclic polyhydric alcohols, or any mixture of these solvents.

A use according to any one of the foregoing embodiments, characterized in that the peptide hydrolysate is used in a quantity of 0.001% to 5% of the total weight of the composition, and preferably in a quantity of 0.01% to 1% of the total weight of the composition.

A use according to one of the foregoing embodiments, characterized in that the composition is in a form suitable for topical application having a physiologically acceptable medium.

A use according to one of the foregoing embodiments, characterized in that the composition furthermore comprises at least one other active agent which protects or improves hair growth and/or health.

A use according to one of the foregoing embodiments to counteract alopecia.

A cosmetic use of a peptide hydrolysate as an active agent as defined in one of embodiments 1 to 3, to strengthen the hair follicle structures.

A use according to embodiment 8, characterized in that the active agent increases the expression of keratin 14 and keratin K17 in the external sheath cells of the hair follicle.

A use according to embodiment 8, characterized in that the active agent increases the expression of collagen IV and protein CD34 in the wall of the hair follicle blood vessels.

A use according to embodiment 8, characterized in that the active agent increases the expression of collagen I in the conjunctive tissue sheath and dermal papilla of the hair follicle.

A method of cosmetic treatment intended to restore and/or stimulate hair growth, or counteract hair loss, characterized in that a composition as defined in one of embodiments 1 to 7 is applied topically to the area being treated.

A method of cosmetic treatment intended to restore and/or stimulate eyelash growth, or counteract eyelash loss, characterized in that a composition as defined in one of embodiments 1 to 7 is applied topically to the area being treated.

A use of a yeast peptide hydrolysate as defined in one of embodiments 1 to 3 as an active agent capable of strengthening and protecting the hair follicle, for the preparation of a dermo-pharmaceutical composition intended to stimulate hair growth or prevent hair loss related to a pathological condition.

A use according to the foregoing embodiments, characterized in that the pathological conditions are alopecia areata, the side effects of drug treatments, and certain infections or inflammations of the scalp.

The disclosure concerns the use of a composition comprising at least one yeast (*Saccharomyces cerevisiae*) peptide hydrolysate as an active agent for strengthening hair and improving hair health. The disclosure may also comprise the use of this novel active agent for making a dermo-pharmaceutical composition intended to stimulate hair growth or to prevent hair loss. The disclosure furthermore refers to a cosmetic treatment method intended to stimulate hair growth or counteract hair loss and counteract external aggressions affecting the hair.

Very many proteins found in plants and yeasts are likely to contain bioactive peptides within their structure. Controlled hydrolysis enables these particular compounds of peptidic nature to be released. It is possible, but not necessary to carry out the disclosure, to extract either the relevant proteins first and then hydrolyze them, or perform hydrolysis first on a crude extract and then purify the peptidic nature compounds.

According to a preferred embodiment, said active principle comes from the hydrolysis of yeast proteins of the *Saccharomyces* species, and preferentially of the *Saccharomyces cerevisiae* species.

Any extraction or purification method known to the person skilled in the art may be used in order to prepare the hydrolysate according to the disclosure.

In a first step, the yeasts are cultured conventionally in a suitable medium for their development, preferably in the presence of lactose. The yeasts are harvested by centrifugation and then suspended in a buffer solution, preferentially a phosphate buffer. In a second step, the cells are burst by using a French press or by using a ball mill, the majority of insoluble membrane components being separated by centrifugation or filtration.

Then proteins are extracted according to the modified conventional method (Osborne, 1924); the plant ground material or yeast lyzate is suspended in an alkaline solution containing an adsorbent product of the insoluble polyvinylpolypyrrolidone (PVPP) type (0.01-20%). Indeed, it was observed that subsequent hydrolysis and purification operations were facilitated by this means. In particular, the concentration of phenolic type substances, interacting with proteins, is markedly reduced.

The soluble fraction, containing proteins, carbohydrates and possibly lipids, is collected after the centrifugation and filtration steps. This crude solution is then hydrolyzed under controlled conditions to generate soluble peptides. Hydrolysis is defined as being a chemical reaction involving cleavage of a molecule by water, this reaction may be done in neutral, acidic or basic medium. According to the disclosure, hydrolysis is carried out chemically and/or advantageously by proteolytic enzymes. The use of plant origin endoproteases (papain, bromelain, ficin) and microorganisms (Aspergillus, Rhizopus, Bacillus, etc.) may then be cited.

For the same reasons as above, i.e., the elimination of polyphenolic substances, a quantity of polyvinylpolypyrrolidone is added to the reaction medium during this controlled hydrolysis step. After filtration, enabling the enzymes and polymers to be eliminated, the filtrate (solution) obtained constitutes a first form of the active principle according to the disclosure.

The hydrolysate obtained at this stage may be purified again in order to select the low molecular weight fractions, preferentially lower than 6 kDa, and more preferentially lower than 5 kDa, and the peptides generated according to their nature. Fractionation may be advantageously carried out by successive ultrafiltration steps through filters of decreasing porosity, by conserving the filtrates at each step and/or by a chromatographic type method. The disclosure carries out a phase of dilution in water or in any mixture containing water, and then sterilization by ultrafiltration in order to obtain a peptidic hydrolysate characterized by a protein content from 0.5 to 5.5 g/l. This peptidic hydrolysate corresponds to the most purified form of the active principle according to the disclosure.

The peptidic hydrolysate obtained according to the disclosure is qualitatively and quantitatively analyzed in high pressure liquid chromatography (HPLC), enabling the proteins having molecular weights from 0.2 to 25 kDa (according to a gradient of appropriate solvents) to be analyzed.

The hydrolysate obtained is composed of peptides with a molecular weight lower than 6 kDa, preferentially lower than 6 kDa.

The second object of the present disclosure is a composition comprising, in a physiologically acceptable medium, the peptidic hydrolysate according to the disclosure as the active principle capable of reinforcing the barrier function of the epidermis.

According to an advantageous embodiment of the disclosure, the active principle according to the disclosure is present in the compositions of the disclosure at a concentration of between approximately 0.0001% and 20%, and preferentially at a concentration of between approximately 0.05% and 5% with relation to the total weight of the final composition.

According to an advantageous embodiment of the disclosure, the active principle according to the disclosure is solubilized in one or more physiologically acceptable solvents, conventionally used by the person skilled in the art, such as water, glycerol, ethanol, propylene glycol, butylene glycol, dipropylene glycol, ethoxylated or propoxylated diglycols, cyclic polyols, white petroleum jelly, vegetable oil or any mixture of these solvents.

In another embodiment of the disclosure there is provided cosmetically and/or pharmaceutically excipients, for example, a cationic and/or an anionic, and/or a neutral hair fixative. PQ-11 is a copolymer of vinyl pyrrolidone (VP) and dimethylaminopropyl methacrylate (DMAEMA). For example, surfactants, such as anionic, cationic or nonionic surfactants may be used, e.g., PEG/PPG-25/dimethicone is a nonionic surfactant, and e.g., Oleth-20 is a non-ionic surfactant. Antimicrobial and/or preservative agents may be used, e.g., diazolidinyl urea and/or iodopropynl butylcarbamate. In another embodiment, a rheological modifier may be used, e.g., sodium polyacrylate and/or hydrogenated polydecene These thicken or increases the viscosity of the formulation. An opacifier may be used, e.g, Styrene/VP copolymer is usually used as a polymeric opacifier, that is, the opacifier makes formulation look white and/or assists in film forming.

According to another advantageous embodiment of the disclosure, the active principle according to the disclosure is previously solubilized in a cosmetic or pharmaceutical carrier such as liposomes, or adsorbed on powdery organic polymers, mineral supports such as talcs and bentonites, and more generally solubilized in, or fixed on, any physiologically acceptable carrier.

The usable composition according to the disclosure may in particular consist of a composition for capillary care, and particularly a shampoo, a conditioner, a treatment lotion, a hairdressing cream or gel, a restructuring lotion for the hair, a mask, etc. The composition may also be present in the form of hair tint or mascara to be applied by brush or comb, in particular onto the eyelashes, eyebrows or hair.

The usable composition according to the disclosure will be applied by any appropriate route, notably oral, parenteral or topical, and the formulation of the compositions will be adapted by the person skilled in the art, in particular for cosmetic or dermatological compositions. Advantageously, the compositions according to the disclosure are intended for topical administration. These compositions therefore must contain a physiologically acceptable medium, i.e., a medium compatible with the skin and epithelial appendages, and must cover all cosmetic or dermatological forms.

It is understood that the active principle according to the disclosure may be used alone or in combination with other active principles.

Advantageously, the usable compositions according to the disclosure may also contain various protective or anti-aging active principles intended to promote and supplement the action of the active principle. In a non-limiting manner, the following ingredients may be cited: cicatrizant, anti-age, anti-wrinkle, smoothing, anti-radical, anti-UV agents, agents stimulating the synthesis of dermal macromolecules or energy metabolism, moisturizing, antibacterial, antifungal, anti-inflammatory, anesthetic agents, agents modulating cutaneous differentiation, pigmentation or depigmentation, agents stimulating nail or hair growth. Preferentially, an agent presenting anti-wrinkle activity, such as an anti-radical or antioxidant agent, or an agent stimulating the synthesis of dermal macromolecules, an agent stimulating energy metabolism, a metalloproteinase inhibitor will be used.

For example, other active principles having an anti-radical or antioxidant action, chosen from among vitamin C, vitamin E, coenzyme Q10, and polyphenolic plant extracts, retinoids, may be added.

The composition according to the disclosure may likewise associate with the active principle according to the disclosure other active principles stimulating the synthesis of dermal macromolecules (laminin, fibronectin, collagen), for example the collagen peptide sold under the name "Collaxyl®" by the Vincience company.

The composition according to the disclosure may also associate with the active principle according to the disclosure other active principles stimulating energy metabolism, such as the active principle sold under the name "GP4G®" by the Vincience company.

Of course, it is obvious that the disclosure is aimed at mammals in general, and more particularly at human beings.

These compositions may particularly be present in the form of an aqueous solution, hydroalcoholic or oily solution; an oil in water emulsion, water in oil emulsion or multiple emulsions; they may also be present in the form of creams, suspensions or else powders, suitable for application on the skin, mucosa, lips and/or epithelial appendages. These compositions may be more or less fluid and have the appearance of a cream, a lotion, a milk, a serum, a pomade, a gel, a paste or a foam. They may also be present in solid form, such as a stick, or may be applied on the skin in aerosol form. They may be used as a care product and/or as a skin makeup product.

All of these compositions also comprise any additive commonly used in the contemplated field of application as well as the adjuvants necessary for their formulation, such as solvents, thickeners, diluents, antioxidants, colorants, sunscreens, self-tanning agents, pigments, fillers, preservatives, fragrances, odor absorbers, other cosmetic active principles, essential oils, vitamins, essential fatty acids, surface active agents, film-forming polymers, etc.

In all cases, the person skilled in the art will make sure that these adjuvants as well as their proportions are chosen so as to not harm the desired advantageous properties of the composition according to the disclosure. These adjuvants may, for example, correspond to a concentration ranging from 0.01 to 20% of the total weight of the composition. When the composition of the disclosure is an emulsion, the fatty phase may represent from 5 to 80% by weight and preferably from 5 to 50% by weight with relation to the total weight of the composition. The emulsifiers and co-emulsifiers used in the composition will be chosen from among those conventionally used in the field under consideration. For example, they may be used in a proportion going from 0.3 to 30% by weight with relation to the total weight of the composition.

The third object of the disclosure is a pharmaceutical composition comprising an effective quantity of peptidic hydrolysate according to the disclosure, as a drug. For example, the pharmaceutical composition may be intended to prevent or treat pathologies characterized by an alteration in the barrier function, such as hypersensitive, irritated or reactive skin and atopic eczema.

According to this form of the disclosure, the compositions will be suitable for oral administration for pharmaceutical use. Thus, the compositions may in particular be present in the form of tablets, capsules, gel capsules, chewable pastes, powders to consume as is or to be mixed immediately before use with a liquid, syrup, gels or any other form known to the person skilled in the art. These compositions also comprise any additive commonly used in the contemplated field of application as well as the adjuvants necessary for their formulation, such as solvents, thickeners, diluents, antioxidants, preservatives, other pharmaceutical active principles, essential oils, vitamins, essential fatty acids, etc.

Particular embodiments of this cosmetic treatment method also result from the previous description. Other advantages and characteristics of the disclosure will more clearly appear upon reading the examples given for illustrative and non-limiting purposes.

EXAMPLE 6

Preparation of a Peptidic Hydrolysate from *Saccharomyces cerevisiae* Yeasts

The peptidic hydrolysate may be obtained from an extract of yeasts from the *Saccharomyces cerevisiae* species. The yeasts are cultivated in a suitable medium for their development, preferably in the presence of lactose, and then centrifuged to recover a biomass. The *saccharomyces* biomass is put in solution in 10 volumes of water in the presence of 2% POLYCLAR® 10 (polyvinylpyrrolidone—PVPP-insoluble) and 0.2% activated carbon. The mixture is adjusted to a pH of between 6 and 7.5 with an aqueous solution of sodium hydroxide 1 M.

After adjustment of the pH, 2% papain is added to the reaction medium. Hydrolysis is obtained after 2 hours of agitation at 55° C. The enzyme is then inactivated by heating the solution to 80° C. for 2 hours. After centrifugation, the reaction mixture corresponding to the *saccharomyces* extract is then obtained. The purification process starts by successive filtrations by using Seitz-Orion filter plates of decreasing porosity (up to 0.2 µm) in order to obtain a bright and clear solution. At this step, the *Saccharomyces* extract is characterized by a dry extract from 25 to 35 g/kg, a protein level from 10 to 15 g/l and a sugar level from 5-10 g/l.

The protein nature of this extract is demonstrated by electrophoresis on polyacrylamide gel. For this analysis, NuPAGE® Bis-Tris Pre-cast (Invitrogen) gels are used. The peptidic hydrolysate is heated to 70° C. for 10 minutes under reducing denaturing conditions in a NuPAGE® LDS sample preparation buffer. A NuPAGE® Antioxidant solution is added into the inner tank (cathode) to prevent the reduced proteins from reoxidizing during electrophoresis. Protein migration is carried out by using the NuPAGE® MES migration buffer with the standard SeeBlue Plus2 as a molecular weight marker. Protein coloration is carried out by using Coomassie Blue® R-250. Under these conditions, 3 large protein families are observed: The $1^{st}$ family corresponds to proteins of molecular weight greater than 75 kDa, the $2^{nd}$ family to proteins from 20 to 25 kDa and the last family to proteins of molecular weight less than 5 kDa.

This solution is then purified by eliminating proteins of molecular weight greater than 5 kDa by using tangential flow filtration.

To do this, the *saccharomyces* peptidic hydrolysate is pumped under pressure through a Pellicon® support equipped with a Pellicon® 2 Biomax cassette 50 kDa. This 1st filtrate is recovered to then be filtered through a second Pellicon® 2 Biomax cassette 10 kDa. A second filtrate is then recovered that is again eluted through a last Pellicon® 2 Biomax cassette 5 kDa. At the end of purification, a beige, bright and clear *saccharomyces* extract is obtained. It is characterized by a dry extract from 35 to 45 g/kg, a protein content from 30 to 40 g/l.

The *saccharomyces* peptidic hydrolysate is then diluted in a mixture water 70%-glycerol 30%, and then sterilization by ultrafiltration in order to obtain a peptidic hydrolysate characterized by a protein content from 0.5 to 5.5 g/l, and preferentially a protein content from 1.5 to 3.5 g/l.

The *saccharomyces* peptidic hydrolysate is then sterilized by ultrafiltration This solution is then analyzed by high pressure liquid chromatography (HPLC) by using an HP1100 apparatus run by the Chem Station software. The column used during elution of the *saccharomyces* hydrolysate is a Nucleosil® 300-5 C4 MPN (125×4 nm) column. This column enables proteins having molecular weights of 0.2 to 25 kDa to be chromatographed (according to a suitable solvent gradient, identical to example 1). Under these chromatographic conditions, several peptidic fractions were isolated.

The determination of the composition in amino acids of the active principle according to the disclosure was also carried out. This is achieved after acid hydrolysis and identification by high pressure liquid chromatography by using pre-derivation with PICT (phenylisothiocyanate).

Embodiments

1. A peptidic hydrolysate characterized in that said peptidic hydrolysate comes from the hydrolysis of yeasts of the *Saccharomyces* genus, and more particularly of the *Saccharomyces cerevisiae* species.

2. The peptidic hydrolysate according to embodiment 1, characterized in that said peptidic hydrolysate contains between 0.5 and 5.5 g/l of peptidic nature compounds.

3. The cosmetic composition comprising, in a physiologically acceptable medium, as an active principle capable of reinforcing the barrier function of the epidermis, the peptidic hydrolysate defined according to one of the previous claims, in a quantity representing from 0.0001% to 20% of the total weight of the composition, and preferentially in a quantity representing from 0.05% to 5% of the total weight of the composition.

4. The composition according to embodiment 3, characterized in that said peptidic hydrolysate is solubilized in one or more physiologically acceptable solvents, such as water, glycerol, ethanol, propylene glycol, butylene glycol, dipropylene glycol, ethoxylated or propoxylated diglycols, cyclic polyols, white petroleum jelly, vegetable oil or any mixture of these solvents.

5. The composition according to embodiment 3 or embodiment 4, characterized in that the composition is present in a form suitable for topical application.

6. The composition according to one of claims embodiments 3, 4, or 5, characterized in that the composition also comprises at least one other active principle promoting the action of said peptidic hydrolysate.

7. A pharmaceutical composition comprising, in a physiologically acceptable medium, the peptidic hydrolysate defined according to any one of embodiments 1, 2, 3, 4, 5, or 6, as a drug.

Hair loss is a natural process in our bodies. The average life of a hair strand is 4.5 years. After this time, it is shed and then replaced by a new hair strand. Approximately 70-100 hairs are shed daily. This type of natural hair shedding takes place when seasons change, in spring and particularly in autumn, when the metabolic rate of the body is higher. In baldness, however, normal replacement does not occur. Thus, baldness is not a problem of hair loss, but a problem of replacement of normal losses.

Hair follicles have three stages: growth, regression and rest. Under normal circumstances, the formation of each hair follicle occurs cyclically, with three stages: anagen, telogen and catagen phases.

Hair strands are produced during the anagen or active growth phase, which consists of growth of the matrix. This phase can be subdivided into proanagen (which sets the start of growth), mesagen and metanagen phases. The anagen phase of the scalp lasts 2-6 years. Approximately 90% of scalp hair strands are in this phase. After that, follicles start their catagen phase, a period of controlled regression/degradation of follicles, which lasts 2-4 weeks. Less than 1% of scalp hairs are in this phase. Finally, follicles start their telogen phase, a state of rest, before cycling back to the anagen phase. This final phase lasts from 2 to 4 months and approximately 10% of hair strands are in this phase. Hair is shed when it reaches the end of this phase, and it is replaced by another hair strand in the same follicle to start a new growth cycle.

The normal rate of production of hair shafts is 0.35 mm/day. It usually ranges from 6 mm to 1.2 mm a month. This speed will depend on the location of the hair follicle, age and sex. As people age, hair tends to grow more slowly.

Hair loss has been a concern for men and women since vanity became a social characteristic. Baldness is by far the commonest cause of hair loss. By the age of 50, it affects approximately 50% of men and 20%-53% of women.

Despite being a benign condition, which does not cause a direct effect on people's health, it significantly affects people's psychological and social well-being. In women, this psychological damage may be even greater, because hair is an important component of women's conception of femininity. Society is prepared to accept bald men, but never bald women. Thus, hair loss becomes a desperate problem for women.

There are several causes of hair loss in women: either a physiological decrease in hair volume after menopause, inadvertent use of chemicals, or a strong genetic predisposition. An association of several factors is also frequent.

The pace of development of baldness is extremely variable. It seems to be determined by the amount of circulating testosterone and the degree of genetic predisposition. The form and extent of hair loss also vary from one individual to another.

A trichogram is also an important exam to assess alopecia. It determines the ratio between the hair growth phases: anagen, catagen and telogen phases. It is used to assess a person's degree of alopecia. A rate below 4.0 of hair in the anagen phase and hair in the telogen phase indicates symptoms of alopecia.

The above-stated conditions are a non-inclusive list of reasons for which a human may wish to use the active ingredient of the disclosure. Other causes of hair loss include A variety of medical conditions can cause hair loss, including: thyroid problems. The thyroid gland helps regulate hormone levels in your body. If the thyroid gland isn't working properly, hair loss may result. This disease occurs when the body's immune system attacks hair follicles—causing smooth, roundish patches of hair loss. Scalp infections, such as ringworm, can invade the hair and skin of the scalp, leading to hair loss. Once infections are treated, hair generally grows back. Diseases that can cause scarring, such as lichen planus and some types of lupus, can result in permanent hair loss where the scars occur. Hair loss can be caused by drugs used to treat cancer, arthritis, depression, heart problems, high blood pressure, or a physical or emotional shock. Many people experience a general thinning of hair several months after a physical or emotional shock. Examples include sudden or excessive weight loss, a high fever, or a death in the family. Hair-pulling disorder, a mental illness, may cause people to have an irresistible urge to pull out their hair, whether it's from the scalp, their eyebrows or other areas of the body. Hair pulling from the scalp often leaves patchy bald spots on the head. Certain hairstyles may also cause hair loss, for example, traction hair loss can occur if the hair is pulled too tightly into hairstyles such as pigtails or cornrows.

In another embodiment of the disclosure, the proteins of the disclosure may be in a cosmetically acceptable or pharmaceutically acceptable composition in an amount, for example a cosmetically effective and/or pharmaceutically effective amount, selected from the following array of numbers, which is in parts per million of a liquid, that is, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000 parts per million. This embodiment of the disclosure includes, without limitation, part per million ranges from any one integer to another integer found in the array of numbers. For example, from the numbers above, the weight of the proteins, in parts per million of the composition may be from about 37 ppm to about 732 ppm by weight, because the numbers are included in the array. Unless otherwise stated in the present specification and claims, any range includes all integers and fractions thereof within the range.

The composition of the disclosure may be used in combination with other alopecia products, for example, minoxidil, finasteride, dutasteride, ketoconazole, spironolactone, and/or flutamide, in clinically effective amounts, or in reduced amounts. For example the composition of the disclosure may work in synergy, or in synergistically effective amounts with one or more of minoxidil, finasteride, dutasteride, ketoconazole, spironolactone, and/or flutamide.

EXAMPLE 7

Two compositions, one with total protein content of from about 5 to 55 ppm of the proteins of Example 6, and a placebo, one without the proteins, were applied in a double blind clinical study to determine the clinical efficacy of the disclosed composition to reduce hair loss and to strengthen hair fibers.

The assessment of the efficacy to reduce hair loss was made with healthy subjects (with no androgenetic alopecia or telogen effluvium) by means of the trichogram technique. The assessment of hair strengthening and likeability was made by applying a sensory questionnaire of perception of efficacy of the products after 30, 60 and 90 days of in-home use.

Ninety-one female subjects volunteered for the study. Seventy eight subjects completed the first part of the study (evaluation after 30 days of product use). Thirteen subjects withdrew for personal reasons not associated with the study before the evaluation after 30 days of product use. Seventy five subjects completed the second part of the study (evaluation after 60 days of product use). Three subjects withdrew from the study for personal reasons unrelated to it before the evaluation after 60 days of products use.

Seventy four subjects completed the study, that is up to a 90 day evaluation. The study was planned and conducted according to established ethical guidelines. The subjects had a condition of normal hair loss (no androgenetic alopecia or telogen effluvium and no systemic pathologies associated to abnormal hair loss). The subjects were instructed to discontinue use of any anti hair loss products on their scalps 48 hours before the start of the study. They were instructed to perform hair coloring procedure only once during the study, which must be held between 45 and 50 days from the beginning of the study.

The study was conducted with 91 healthy subjects split into two study groups: Forty six subjects used the placebo product) and forty five subjects used the active product).

The assessments included an analysis of the amount of anagen and telogen hair strands via a trichogram technique and subjective assessment by the subjects about their perception of efficacy of the products being studied after 30, 60 and 90 days of in-home use.

The diagnosis via trichogram provided quantitative information about subjects' hair growth and hair fall. is the trichograms analysis was used to assess a subject's degree of alopecia. It was used to assess the ratio of anagen hair strands (A) in comparison to the individual's telogen strands (T). Anagen hair strands are in the growth phase and telogen strands are in the involution phase. An A/T ratio equal to or above 4.0 indicates that the individual's hair loss is considered normal. If this ratio is below 4.0, this is an indication of pathological hair fall (telogen effluvium or alopecia). On the first day of the study, 50 strands of hair were randomly plucked from the scalp of each subject. The strands collected were placed on glass blades for microscopy and then analyzed with an optical microscope, model Digitron® 3000 (Castells, Brazil). The aspect of the bulb was analyzed to determine the stage in the strand's lifecycle, and the number of strands in the telogen and anagen phase was recorded.

Only subjects who had normal hair fall were included. Normal hair fall was characterized as the ratio between strands in the anagen and in the telogen phase s (A/T) equal to or above 4.0. The volunteers were instructed to use the products for 90 days, according to the mode of use submitted by the sponsor and described in the Term of Free Informed Consent (TFIC), After 30, 60 and 90 days of use of the products the examination of trichogram was performed. This assessment included a collection of data on habits of consumption of hair care products and the physiological characteristics of the hair of the subjects who joined the study.

This assessment was guided by the pre-study model questionnaire was conducted as such: The assessment of perceived efficacy and likeability was made by applying a questionnaire after the study. This questionnaire was completed by the subjects after they used the products at home for 30, 60 and 90 days.

The questionnaire was structured with statements relating to the mode of application, the sensorial aspect, perceived efficacy and likeability, considering the scores given in a hedonic, 5-point scale where 1 meant complete disagreement with the statement and 5 meant complete agreement with the statement. Final opinions on what subjects liked or disliked about the product were also collected.

The questionnaire was answered in a confidential and individual manner with no interference of the researcher or other subjects. Before applying the questionnaire, the researcher explained the meaning of each statement in the questionnaire. Data analysis was conducted using Microsoft® Office Excel 2003 (Microsoft Corp., USA, 2003) and statistical analysis was conducted using GraphPad™ Prism® 4.03 (GraphPad Software, San Diego Calif. USA, www.graphpad.com).

Assessment of A/T ratio with the trichogram technique was done as follows. The diagnosis with a trichogram technique may supply quantitative information on hair growth and fall. The analysis by trichogram includes an assessment of the rate of the person's anagen (A) and telogen (T) hair strands, to provide information on the proportion of hair strands in each phase of the lifecycle. Such analysis provided the data in FIG. 3.

By the term Conditioning Milk Spray, F#11994-20 is meant the protein composition, or active ingredient composition. By the term Conditioning Milk Spray, F#11994-22 is meant the placebo composition, or the composition without the protein.

FIG. 1 shows that the A/T ratio for the group using active ingredient, increased progressively during the study.

The group that used the placebo composition showed a small fluctuation in the A/T ratio during the study, presenting slightly lower values in the evaluations after 30, 60 and 90 days of use, when compared to the baseline.

After 30 days of product use, 36% of the subjects who used the placebo composition had some improvement in the A/T ratio, whereas 63% of the subjects who used the active ingredient had an improvement in the A/T ratio, when compared to the baseline values.

After 60 days of product use, 44% of the subjects who used the placebo composition had some improvement in the A/T ratio, whereas 86% of the subjects who used the active ingredient had an improvement in the A/T ratio, when compared to the baseline values.

After 90 days of product use, 41% of the subjects who used the placebo composition had some improvement in the A/T ratio, whereas 83% of the subjects who used the active ingredient had an improvement in the A/T ratio, when compared to the baseline values.

For the significance assessment of the variation in the A/T ratio observed by the use of the samples, the values calculated for the baseline A/T ratio (before the treatment) were statistically compared to the A/T values obtained after 30, 60 and 90 days of the products use, via the paired Student's t-test, with 95% confidence interval. According to the results obtained, it was possible to conclude that for the placebo composition, the A/T ratio obtained after 30, 60 and 90 days had no statistical difference (P>0.05) when compared to the baseline values (before the treatment).

However, for the active ingredient composition:

There was a statistically significant increase (P<0.05) in the A/T ratio obtained after 30, 60 and 90 days in comparison to the baseline values (before the treatment);

There was a statistically significant increase (P<0.05) in the A/T ratio obtained after 60 and 90 days in comparison to the values obtained after 30 days of the product use; and There was no statistical difference (P>0.05) in the A/T ratio obtained after 60 days in comparison to the values obtained after 90 days of the product use.

To assess the comparison between the products, the coefficient between the A/T ratio obtained in 30, 60 or 90 days of evaluation and the baseline A/T ratio, called $C_{A/T}$, was obtained for both samples, as described in Equation 1:

$$CA/T = (A/T)tj/(A/T)ti, \text{ where } i=\text{baseline and } x=30, 60 \text{ or } 90 \text{ days.} \qquad \text{Equation 1}$$

The values for $C_{A/T}$ of both products were statistically compared using a nonparametric Student's t-test, considering a 95% confidence interval. The results of this analysis are described in full in Appendix VIII. According to the results, it was possible to observe that the active ingredient significantly increased the A/T ratio (P<0.05) compared to the placebo after 30, 60 and 90 days of use.

Assessment of the profile of the study panel was conducted in the following manner. In this assessment, data were collected on the profile of consumption and habits related to the use of hair care products as well as physiological characteristics of hair and scalp of the study subjects. The diagnosis via trichogram examination showed that, after 90 days of in-home use per directions described in this report of the samples the active ingredient composition and the placebo composition:

There was a statistically significant increase of the anagen/telogen ratio in the group of subjects who used the active ingredient composition after 30, 60 and 90 days of use. This indicates that the product was effective to reduce hair loss. This effect was perceived in 63% of the subjects in the evaluation of 30 days, in 86% of the subjects in the evaluation of 60 days and in 83% of the subjects in the evaluation of 90 days.

There were no statistically significant changes in the anagen/telogen ratio in the group of subjects who used the placebo composition after 30, 60 and 90 days of use. This indicates that the hair loss for this study group had no significant changes caused by the use of the product.

In the comparison between the products under study, it was observed a significant increasement of anagen/telogen ratio delivered by the active ingredient in comparison to the placebo in the evaluation of 30, 60 and 90 days after using the products.

Also it was possible to observe the following results though the perceived efficacy and likeability conducted after 90 days of use:

The active ingredient composition provided the following indications:

97.1% of the subjects thought that the product is easy to apply onto the scalp;

100.0% of the subjects thought that the product spread evenly on the scalp;

94.3% of the subjects thought that the product was absorbed quickly in the scalp;

100.0% of the subjects thought that the product worked well with the hair regimen (shampoo, conditioner) used;

97.1% of the subjects felt the scalp moisturized;

97.1% of the subjects thought that the product made the hair roots stronger;

62.9% of the subjects thought that the product didn't make the scalp greasy;

94.3% of the subjects thought that the product reduced hair fall while combing, drying or styling hair;

94.3% of the subjects thought that the product prevented hair fall during washing;

94.3% of the subjects thought that the product prevented hair fall on the pillow;

94.3% of the subjects thought that the product prevented hair breakage;

80.0% of the subjects thought that the product left hair thicker;

88.6% of the subjects thought that the product left hair denser and fuller;

100.0% of the subjects thought that the product left hair stronger;

97.1% of the subjects thought that the product left hair healthier;

97.1% of the subjects thought that the product left hair shinier;

97.1% of the subjects thought that the product made the hair look smoother;

97.1% of the subjects liked the product; and 91.4% of the subjects would use this product in the future.

The placebo composition provided the following indications:

94.9% of the subjects thought that the product is easy to apply onto the scalp;

94.9% of the subjects thought that the product spread evenly on the scalp;

100.0% of the subjects thought that the product was absorbed quickly in the scalp;

100.0% of the subjects thought that the product worked well with the hair regimen (shampoo, conditioner) used;

92.3% of the subjects felt the scalp moisturized;

92.3% of the subjects thought that the product made the hair roots stronger;

43.6% of the subjects thought that the product didn't make the scalp greasy;

92.3% of the subjects thought that the product reduced hair fall while combing, drying or styling hair;

89.7% of the subjects thought that the product prevented hair fall during washing;

94.9% of the subjects thought that the product prevented hair fall on the pillow;

92.3% of the subjects thought that the product prevented hair breakage;

71.8% of the subjects thought that the product left hair thicker;

69.2% of the subjects thought that the product left hair denser and fuller;

92.3% of the subjects thought that the product left hair stronger;

92.3% of the subjects thought that the product left hair healthier;

64.1% of the subjects thought that the product left hair shinier;

71.8% of the subjects thought that the product made the hair look smoother;

97.4% of the subjects liked the product;

84.6% of the subjects would use this product in the future;

During the study period no symptoms or signs of allergic reaction or discomfort to the use of the products under study were observed or reported by the subjects.

The following references were used as technical references to assist in the study; all of which are incorporated by refernence herein and relied upon: Mansur MCA. O cabelo, os andrógenos e a alopecia androcronogenética;

Tese Doutorado, UFRJ, Rio de Janeiro 172 p. 1989;

Fitzpatrick T B et al. Dermatology in General Medicine. $4^a$ ed. 2 vol. New York: McGraw-Hill, 1993;

Rook A et al. testbook of Dermatology, $6^a$ ed. London: Blackwell Science, 1998. Quiroga M I, Guillot C F. Cosmetica Dermatológica Prática, $4^a$ ed. Buenos Aires: El Ateneo, 1973; and Pereira, J M. O Tricograma—Significado e método de realização. An. Bras. Dermatol, 68 (3), 145-152, 1993.

Active ingredient formulation was as in FIG. 2.

The invention claimed is:

1. A method of attenuating hair loss in a human in need thereof comprising:
topically applying to skin comprising hair follicles of the human in need thereof a composition comprising:
an effective amount of a hair-loss attenuating peptide hydrolysate, wherein the peptide hydrolysate is produced from a protease hydrolysis of a protein-rich filtrate collected after cell disruption and elimination by centrifugation or filtration of most of the insoluble membrane components of a *Saccharomyces* yeast culture, wherein the protein-rich filtrate collected is thereafter adjusted to a generally neutral pH and hydrolyzed by a proteolytic enzyme, and wherein the peptide hydrolysate is composed of peptides each having a molecular weight of less than 6000 Daltons, and
a cosmetically acceptable carrier;
wherein the proteolytic enzyme is selected from papain, bromelain, and ficin or extracted from a microorganism selected from *aspergillus, rhizopus*, and *bacillus;*
wherein the peptide hydrolysate increases the expression of keratin 14 in the external sheath cells of hair follicles, increases the expression of collagen IV in the wall of hair follicle blood vessels, increases the expression of protein CD34 in the wall of hair follicle blood vessels, and/or increases the expression of collagen I in the conjunctive tissue sheath and dermal papilla of the hair follicle.

2. The method according to claim 1 wherein the effective amount of the hair-loss attenuating peptide hydrolysate present in the composition is from about 5 to 55 parts per million.

3. The method according to claim 1 wherein the hair-loss attenuating peptide hydrolysate is composed of peptides each having a molecular weight less than 5000 Daltons.

4. The method according to claim 1 wherein the composition is a liquid.

5. The method according to claim 1 wherein the composition is a gel.

6. The method according to claim 1 further comprising applying the composition daily.

7. The method according to claim 6 further comprising applying the composition in an amount effective to increase, on average among a population of persons on whom the composition is applied, an average anagen/telogen ratio of hair from about 10 to about 14 over about 90 days of application.

8. The method according to claim 6 further comprising applying the composition in an amount effective to increase, on average among a population of persons on whom the composition is applied, an average anagen/telogen ratio of hair from about 10 to about 13.8 over about 60 days of application.

9. The method according to claim 6 further comprising applying the composition in an amount effective to increase, on average among a population of persons on whom the composition is applied, an average anagen/telogen ratio of hair from about 10 to about 12 or more over about 30 days of application.

10. The method of claim 1, wherein the hydrolysis by the proteolytic enzyme proceeds for about two hours at a temperature of about 55° C.

11. The method of claim 1, wherein the effective amount of a hair-loss attenuating peptide hydrolysate is about 0.05% to about 5% by weight of the composition.

12. The method of claim 1, wherein the *Saccharomyces* yeast culture is a *Saccharomyces cerevisiae* yeast culture.

13. The method of claim 1, wherein the effective amount of a hair-loss attenuating peptide hydrolysate is 1% by weight of the composition and the composition is applied to a scalp five days per week over a thirty day period.

14. The method of claim 13, wherein about eight grams of the composition is topically applied per day of the five days.

15. A method of attenuating hair loss in a human in need thereof comprising:
topically applying to skin comprising hair follicles of the human in need thereof a composition comprising:
about 0.05% to about 5% by weight of the composition of a hair-loss attenuating peptide hydrolysate, wherein the peptide hydrolysate is produced from a protease hydrolysis of a protein-rich filtrate collected after cell disruption and elimination by centrifugation or filtration of most of the insoluble membrane components of a *Saccharomyces cerevisiae* yeast culture, wherein the protein-rich filtrate collected is thereafter adjusted to a generally neutral pH and hydrolyzed by a proteolytic enzyme at a temperature of about 55° C. for about two hours, and wherein the peptide hydrolysate is composed of peptides each having a molecular weight of less than 6000 Daltons, and
a cosmetically acceptable carrier;
wherein the proteolytic enzyme is selected from papain, bromelain, and ficin or extracted from a microorganism selected from *aspergillus, rhizopus*, and *bacillus*.

* * * * *